(12) United States Patent
Radl et al.

(10) Patent No.: US 11,246,580 B2
(45) Date of Patent: Feb. 15, 2022

(54) CANTILEVER LIVER RETRACTION DEVICES AND METHODS OF USE

(71) Applicant: Boehringer Technologies, LP, Phoenixville, PA (US)

(72) Inventors: Christopher L. Radl, Malvern, PA (US); Steven C. Moulden, West Chester, PA (US); William Charles Dackis, Philadelphia, PA (US)

(73) Assignee: Boehringer Technologies, LP, Phoenixville, PA (US)

( * ) Notice: Subject to any disclaimer, the term of this patent is extended or adjusted under 35 U.S.C. 154(b) by 123 days.

(21) Appl. No.: 16/856,385

(22) Filed: Apr. 23, 2020

(65) Prior Publication Data

US 2020/0345339 A1 Nov. 5, 2020

Related U.S. Application Data

(60) Provisional application No. 62/840,618, filed on Apr. 30, 2019, provisional application No. 62/915,108, filed on Oct. 15, 2019.

(51) Int. Cl.
*A61B 17/02* (2006.01)

(52) U.S. Cl.
CPC ...... *A61B 17/0206* (2013.01); *A61B 17/0281* (2013.01)

(58) Field of Classification Search
CPC . A61B 17/02; A61B 17/0206; A61B 17/0281; A61B 17/0218; A61B 2017/0225
(Continued)

(56) References Cited

U.S. PATENT DOCUMENTS

| 5,505,689 A | 4/1996 | Kramer et al. |
| 6,221,008 B1 | 4/2001 | Keckstein et al. |

(Continued)

FOREIGN PATENT DOCUMENTS

EP 0720446 B1 8/2002

OTHER PUBLICATIONS

Newly Developed Liver-Retraction Method For Laparoscopic Gastric Surgery Using a Silicone Disc: The φ-Shaped Technique, by Hiroshi Saeki, MD, et al. appearing on pp. e43-e46 of Journal Of American College Of Surgeons © 2013.

(Continued)

*Primary Examiner* — Eduardo C Robert
*Assistant Examiner* — Christina Negrellirodriguez
(74) *Attorney, Agent, or Firm* — Caesar Rivise, PC

(57) ABSTRACT

Intra-abdominal liver retraction devices and methods of use. One device includes a body, a stabilizing member, and a lifting filament. The stabilizing member is configured to be swiveled so that the device can be introduced through a trocar into the abdomen of a patient. The filament pulls the stabilizing member into engagement with the abdominal wall while a foot section lifts the liver. Another device includes first, second and third sections coupled together by a filament. The first and second sections are pivotably connected by a first pivotable joint. The second and third sections are pivotably connected by a second pivotable joint including the flexible filament. The second and third sections are pivoted with respect to each other to form a support surface to lift the liver by pulling the filament. The second pivotable joint separates to enable the device to be removed.

40 Claims, 8 Drawing Sheets

(58) Field of Classification Search
USPC .......................................................... 600/206
See application file for complete search history.

(56) References Cited

U.S. PATENT DOCUMENTS

| | | | |
|---|---|---|---|
| 8,449,461 B2 * | 5/2013 | Kim | A61B 17/0218 600/210 |
| 8,795,166 B2 | 8/2014 | Roth et al. | |
| 9,974,532 B2 | 5/2018 | Baas et al. | |
| 2005/0240083 A1 | 10/2005 | Orban, III | |
| 2008/0081945 A1 | 4/2008 | Toso et al. | |
| 2009/0137877 A1 | 5/2009 | Minnelli et al. | |
| 2009/0171143 A1 | 7/2009 | Chu et al. | |
| 2009/0221868 A1 | 9/2009 | Evans | |
| 2011/0040152 A1 | 2/2011 | Kim et al. | |
| 2018/0263613 A1 | 9/2018 | Wik et al. | |

OTHER PUBLICATIONS

International Search Report for PCT/US2020/030249 dated Aug. 13, 2020.

* cited by examiner

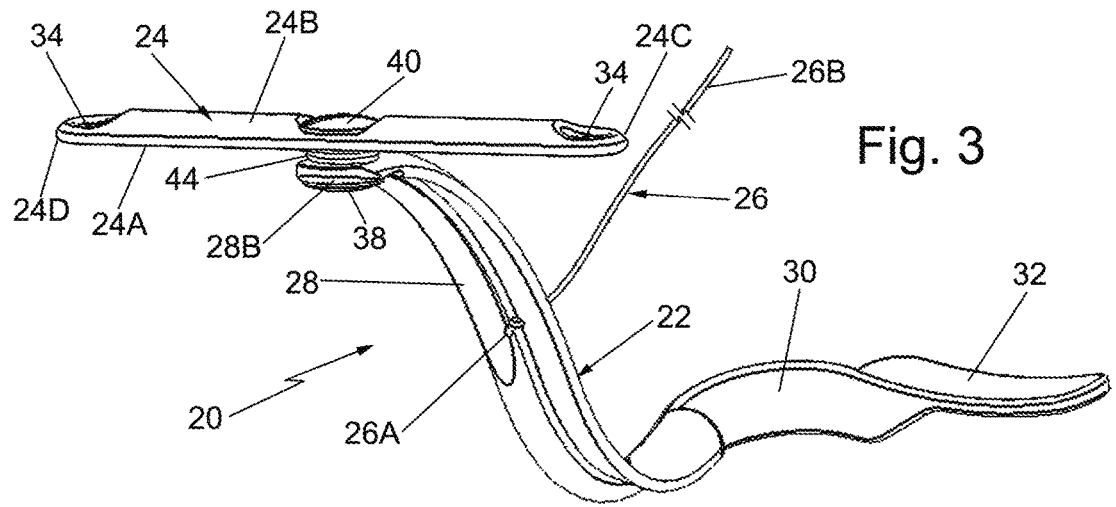
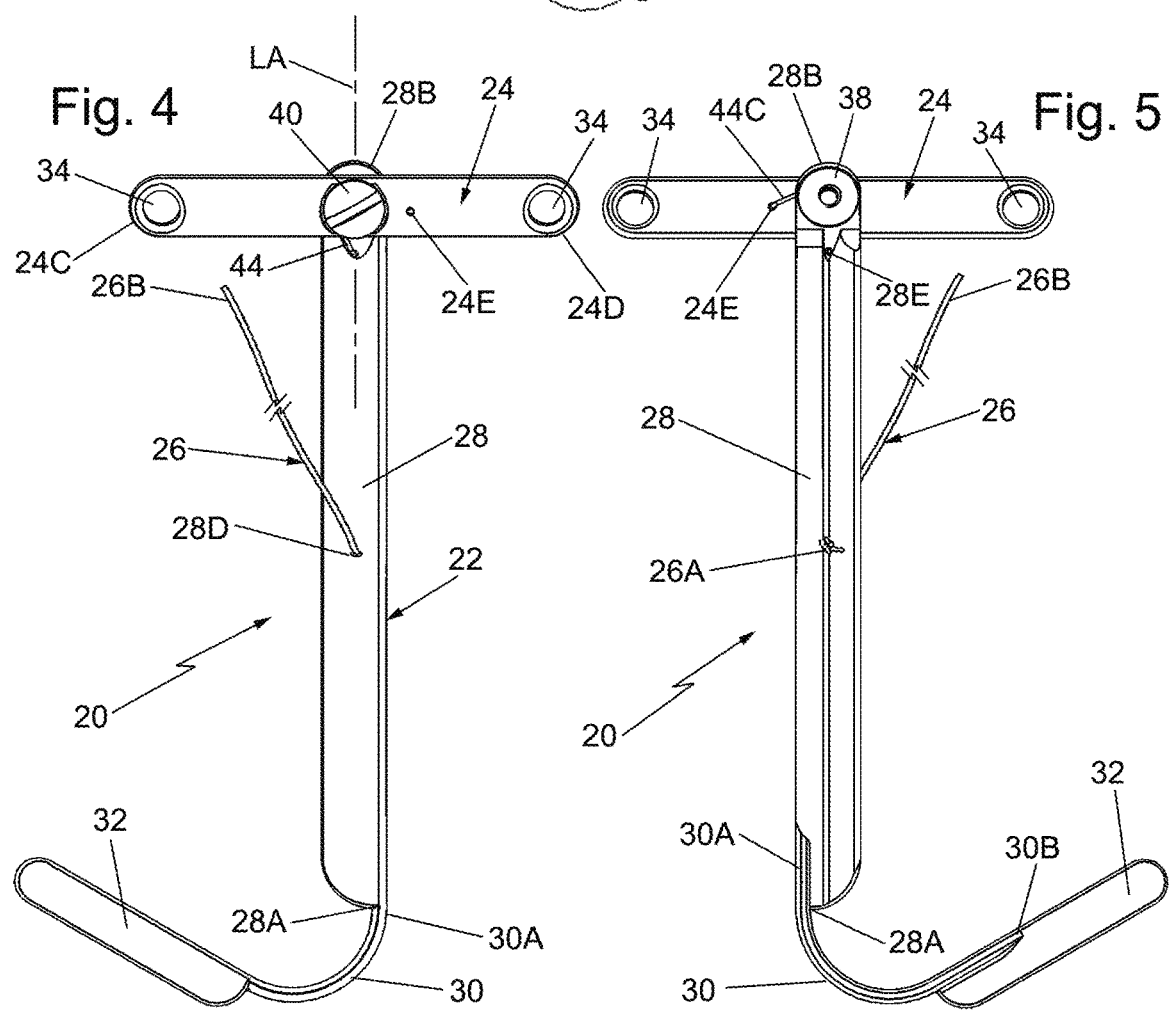

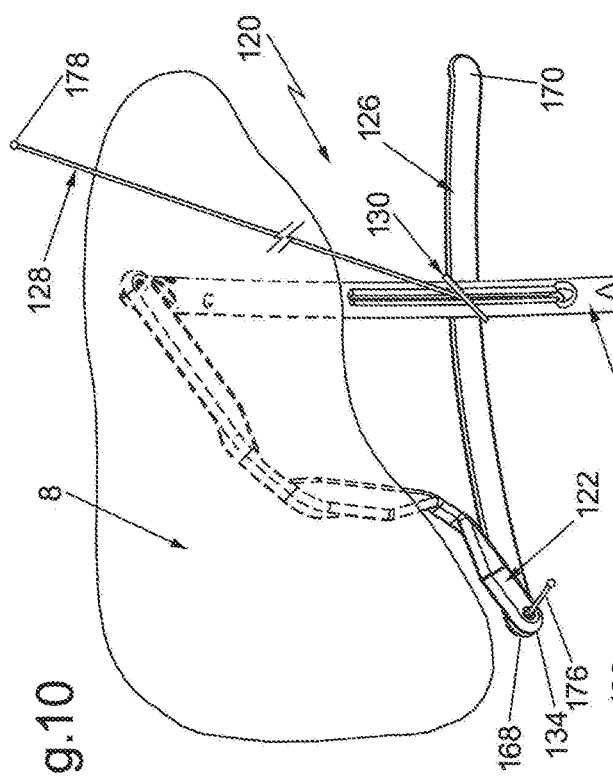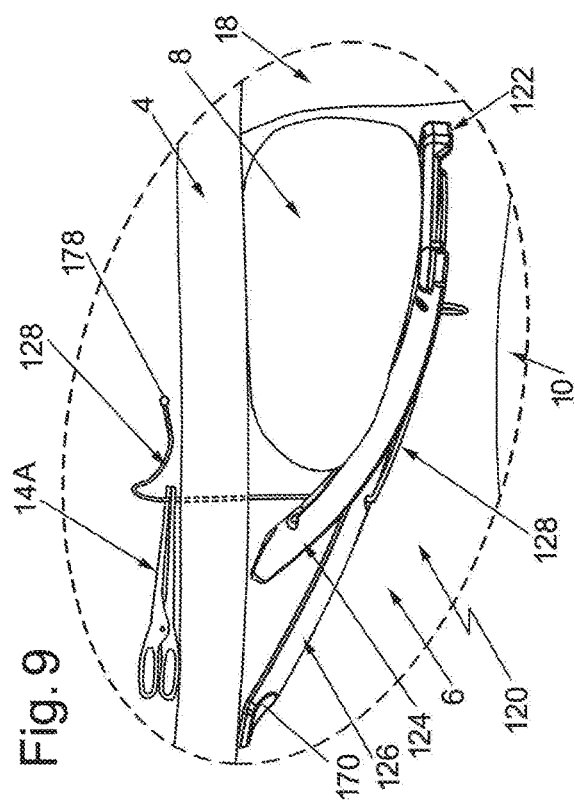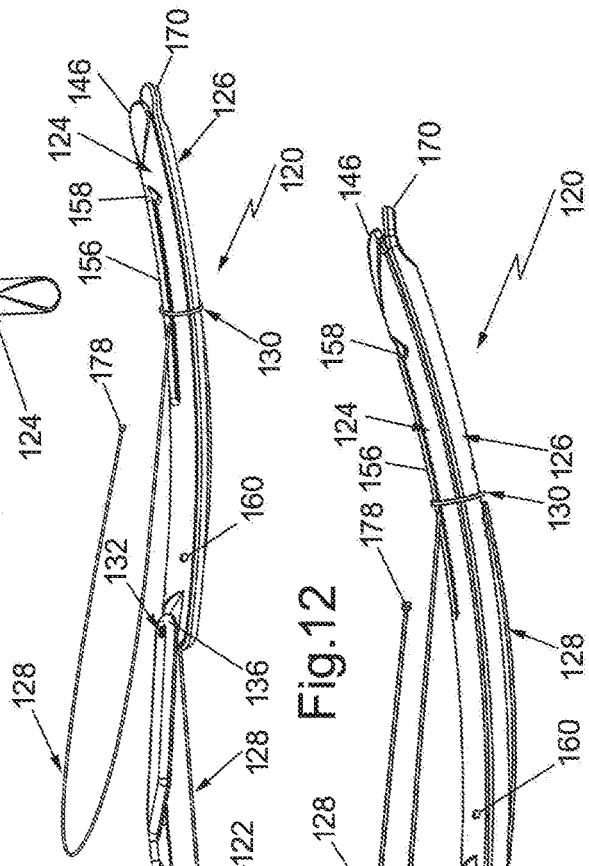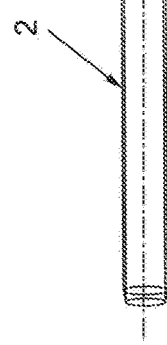

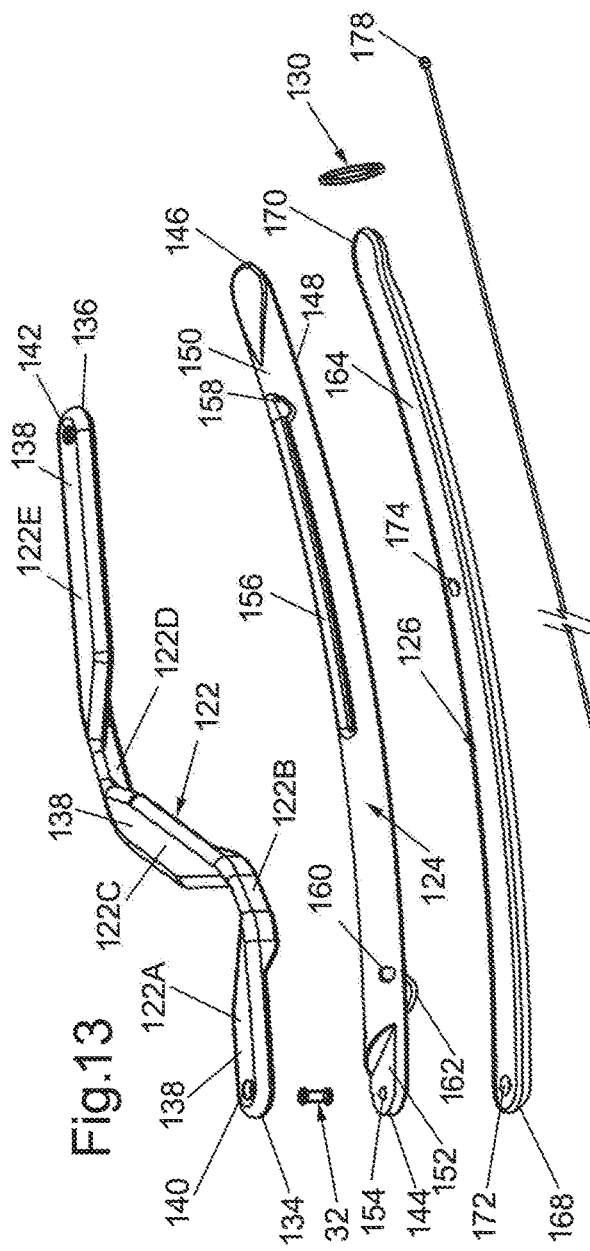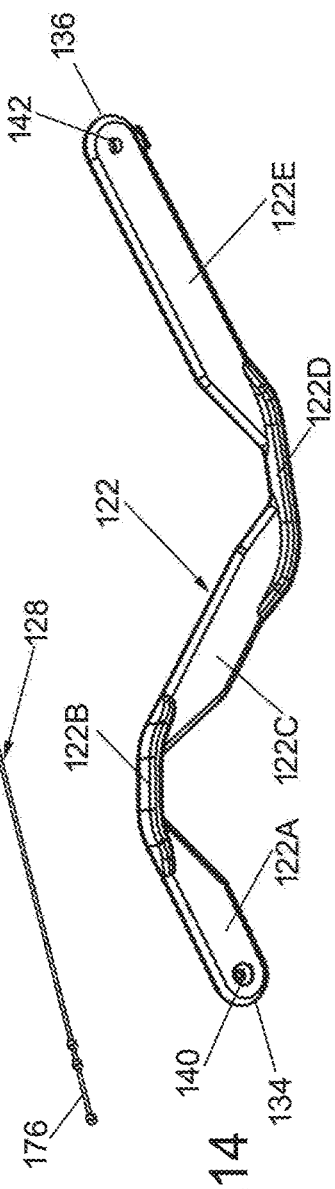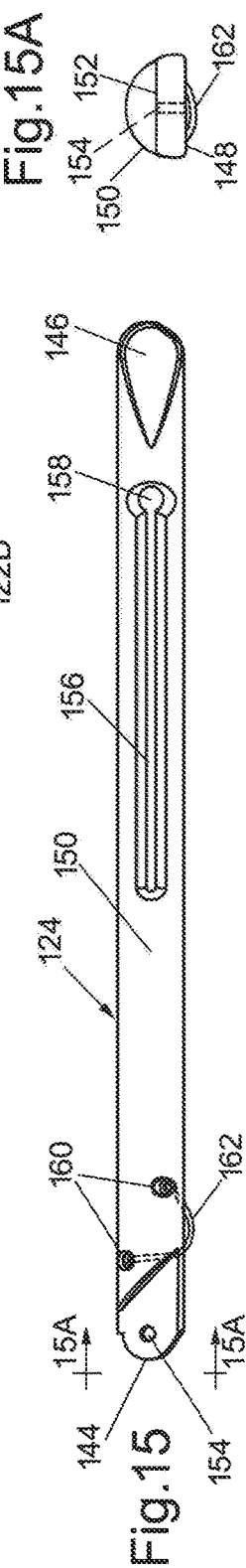

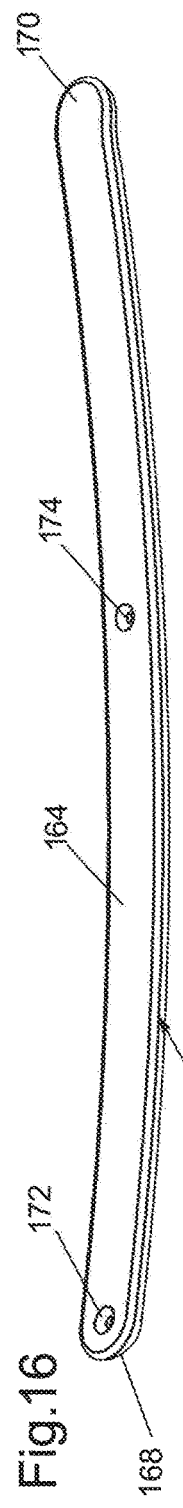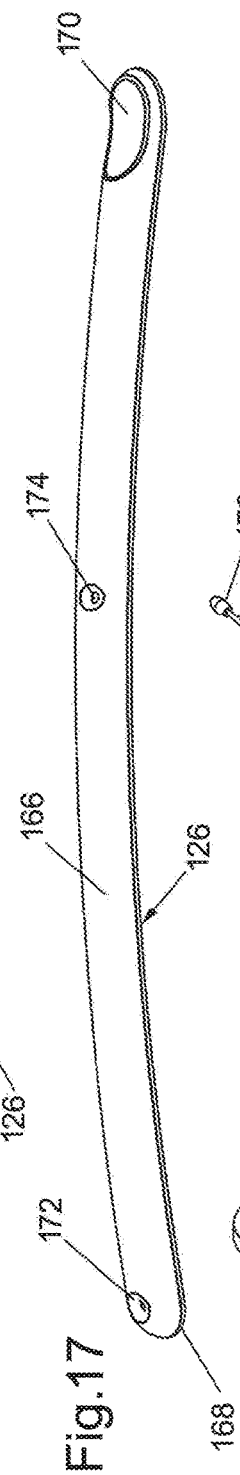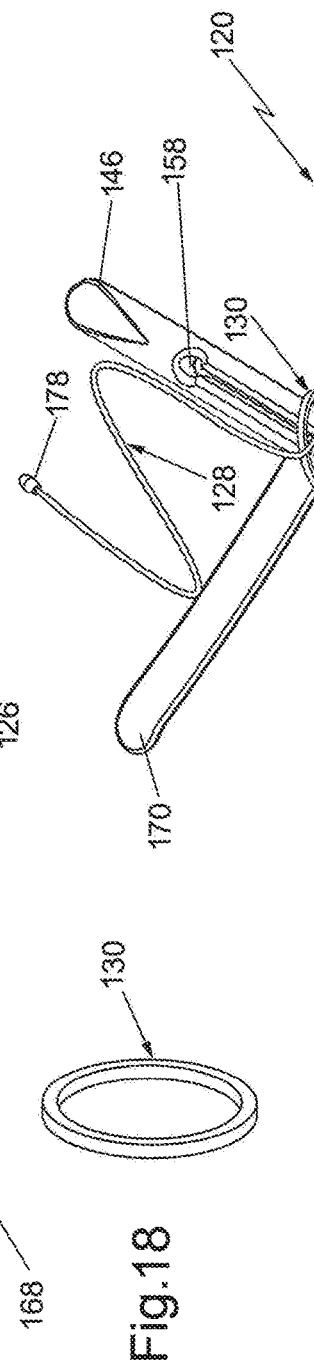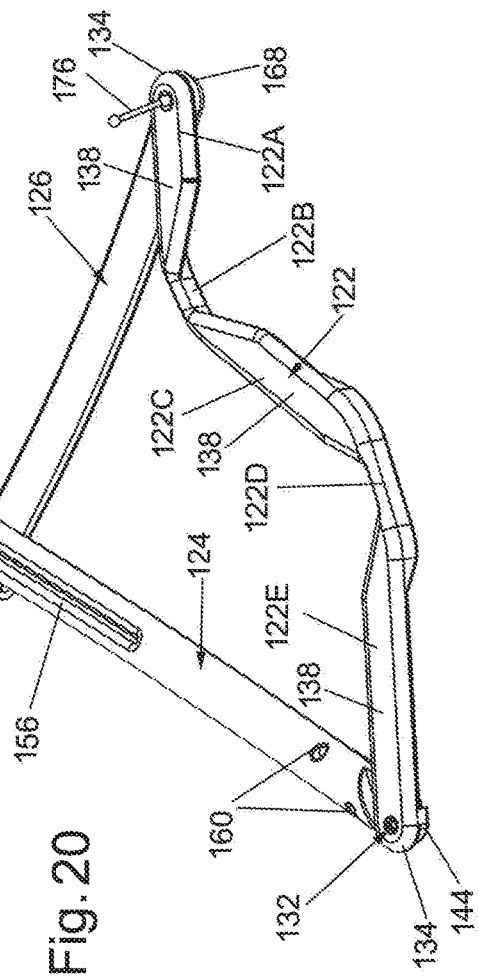

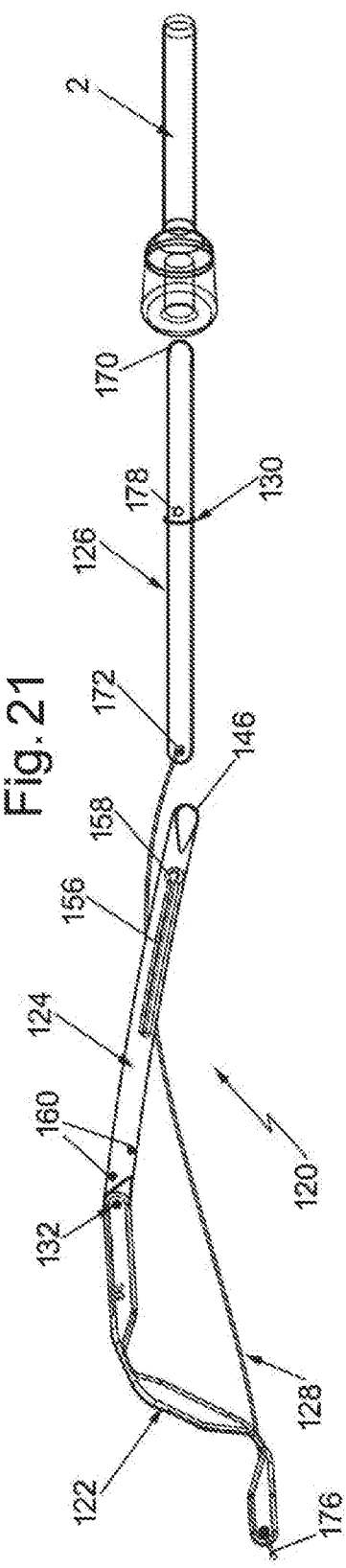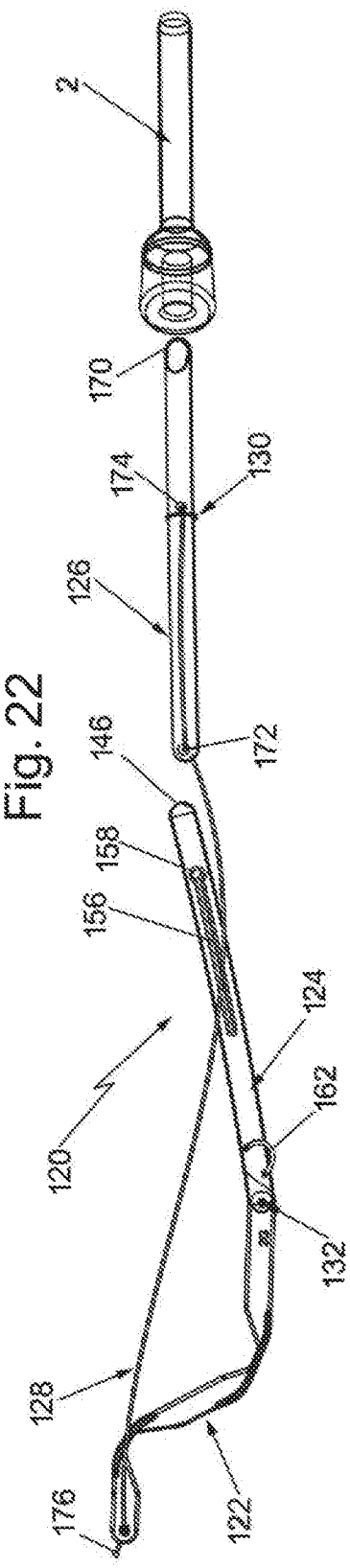

CANTILEVER LIVER RETRACTION DEVICES AND METHODS OF USE

CROSS-REFERENCE TO RELATED APPLICATIONS

This utility application claims the benefit under 35 U.S.C. § 119(e) of Provisional Application Ser. No. 62/840,618 filed on Apr. 30, 2019, entitled Cantilever Liver Retraction Device and Method of Use, and Provisional Application Ser. No. 62/915,108 filed on Oct. 15, 2019, entitled Liver Retraction Device and Method of Use. The entire disclosures of both of those provisional applications are incorporated by reference herein.

FIELD OF THE INVENTION

This invention relates generally to medical devices and methods of use and more particularly to devices and methods for lifting the liver or other organ in a patient during a laparoscopic procedure.

SPECIFICATION

Background of the Invention

During laparoscopic procedures in the abdomen an instrument, e.g., a grasper or retractor, may be used to lift or otherwise move an organ to a position so that it does not interfere with the laparoscopic procedure on another organ or anatomic structure/tissue (the "target") within the abdomen. The organ to be moved or lifted is susceptible to being scraped, punctured, bruised or otherwise damaged using the conventional retractors, clamps or graspers during laparoscopic surgical procedures to move it while the surgeon works on the target. This is particularly true of the liver. Thus some retractors include inflatable balloons and the like so to avoid unintentional damage to the organ being moved. However, such retractors are rather large and hence may block the field of view of the surgeon.

U.S. Pat. No. 8,449,461 (Kim et al.) discloses a surgical retractor capable of preventing an organ of a human body from being damaged when the organ of the human body positioned over a surgical area in the human body is lifted up. The surgical retractor includes a support body including a plurality of support members that are inserted below the organ to lift it upward. The plurality of support members are fastened to a joint, and a protective film member joined to the support body to cover a region between the support members, and configured to enclose and protect a lower surface of the organ.

U.S. Pat. No. 9,974,532 (Baas et al.) discloses a clip for organ retraction during minimally invasive surgery. The clip comprises a body made of a biocompatible material. The body comprises at least two generally opposing first and second segments that form a jaw defined by a separation between the two segments. The two segments each comprise distal and proximal ends wherein the proximal ends may be directly connected or connected through one or more segments within the body of the clip and wherein the clip defines at least four configurations a resting configuration, an open configuration, a grabbing configuration, and a sliding configuration. One embodiment is in the form of a system comprising a plurality of clips wherein each clip is attached to a band and wherein the bands can attach to each other to form a net for moving an organ or tissue.

United States Published Application 2009/0221868 (Evans) discloses a sling anchor system for implanting support members in patients. The system includes a support member, such as a sling for urinary incontinence, tissue anchors, filamentary elements for associating the support member with the anchors, and introducer needles for placing the anchors in a patient. The support members can also be configured for use in pelvic floor repair, such as for treating cystoceles, rectoceles, and enteroceles.

United States Published Application 2018/0263613 (Wik et al.) discloses an organ retraction device for use during laparoscopic surgery. The device is in the form of a triangular fabric sling which is reinforced about its periphery. The sling has a curved needle connected to a first end of the sling by a first suture having one point of attachment to the sling and a straight needle connected to the second end of the sling by a second suture having two points of attachment on the sling. The sling is configured to support the liver of a patient in a "hammock" type structure during the procedure with the curved needle attached to the diaphragm of the patient and with the straight needle placed through the abdominal wall.

The patent literature includes disclosures of other sling or similar devices for use in the body of a patient for supporting tissue therein, such as: US2008/0081945 (Toso et al.); US2009/0137877 (Minnelli et al.); and US2009/0171143 (Chu et al.)

In a paper entitled "Newly Developed Liver-Retraction Method For Laparoscopic Gastric Surgery Using A Silicone Disc: The ϕ-Shaped Technique", by Hiroshi Saeki, M D, et al. appearing on pages e43-e46 of Journal Of American College Of Surgeons©2013, there is disclosed a leaf shaped silicone disc having a flexible shape-memory frame for lifting the lateral segment of the liver of a patient. In particular, the procedure disclosed entails: (a) creating a small loop at the distal end of a 2-0 monofilament suture; (b) lifting up the lateral segment of the liver with forceps, and suturing one of the diaphragmatic crura; (c) cutting the suture needle extracorporeally; (d) passing the proximal end of the suture through the loop; (e) introducing the loop into the abdominal cavity and fixing it at the crus of the diaphragm; (f) passing the proximal end of the suture through two holes of the silicone disc, extracorporeally, across the desired disc axis; (g) introducing the silicone disc into the abdominal cavity and placing it under the liver, with the suture side down, (h) pulling the suture through the epigastrium; and (i) applying traction to the suture to allow the silicone disc to lift the lateral segment of the liver.

While the above identified prior art appears generally suitable for their intended purposes, they nevertheless leave something to be desired from one or more various structural and/or operational standpoints. For example, some of the prior art devices require anchoring the device to the patient's diaphragm by means of some type of piercing element.

Thus, a need exists for a device which can be used during laparoscopic surgery to support a body organ, such as the liver, without injuring it, yet which is simple in construction, low in cost, easy to use, effective, does not appreciably decrease the area of the surgical site and the field of view of the surgeon and does not require anchoring to the diaphragm of the patient. The subject invention addresses that need.

BRIEF SUMMARY OF THE INVENTION

One aspect of this invention is an intra-abdominal liver retraction device for use in a patient having a liver, an abdomen, an abdominal wall and a diaphragm. The intra-abdominal liver retraction device comprises a generally J or L shaped body, a stabilizing member and a lifting or elevating filament. The generally J or L shaped body includes an elongated section, an intermediate section, and a foot section. The elongated section has a proximal end. The foot section extends at an angle to the elongated section and is configured to be brought to a position adjacent to a portion of the diaphragm of the patient, whereupon a portion of the elongated section and the foot section is disposed under a portion of the liver. The stabilizing member has a pair of ends disposed opposite each other. The stabilizing member is coupled to the proximal end and configured to be moved with respect thereto from a first orientation to a second orientation and vice versa. The stabilizing member when in the first orientation extends generally perpendicular to the elongated section. The stabilizing member when in second orientation extends generally parallel to the elongated section. The stabilizing member is configured to be brought into frictional engagement with a portion of the abdominal wall of the patient. The flexible filament is connected to the elongated section of the generally J or L shaped body and is configured to be drawn from within the abdomen through an aperture in the abdominal wall to cause the stabilizing member when in the first orientation to be brought into frictional engagement with a portion of the abdominal wall and also cause the elongated section and the foot section to lift the liver upward towards the abdominal wall.

In accordance with one preferred aspect of the intra-abdominal liver retraction device of this invention, the generally J or L shaped body is somewhat flexible, yet self-supporting and configured such that when the stabilizing member is in the second orientation the intra-abdominal liver retraction device can be bent into a somewhat linear shape for insertion through a trocar into the abdomen.

In accordance with another preferred aspect of the intra-abdominal liver retraction device of this invention, the intermediate section is located between the elongated section and the foot section.

In accordance with another preferred aspect of the intra-abdominal liver retraction device of this invention, the device comprises a swivel member coupled between the proximal end and the stabilizing member to enable the stabilizing member to be swiveled to either the first or second orientations.

In accordance with another preferred aspect of the intra-abdominal liver retraction device of this invention, the stabilizing member is normally biased into the first orientation.

In accordance with another preferred aspect of the intra-abdominal liver retraction device of this invention, the device additionally comprises a spring for normally biasing the stabilizing member into the first orientation.

In accordance with another preferred aspect of the intra-abdominal liver retraction device of this invention, the foot section is an elongated slightly concave member.

In accordance with another preferred aspect of the intra-abdominal liver retraction device of this invention, the elongated section has a predetermined maximum width, wherein the stabilizing member is an elongated member having a predetermined maximum width, wherein the foot section has a predetermined maximum width, and wherein the predetermined maximum width of the elongated section, the predetermined maximum width of the stabilizing member and the predetermined maximum width of the foot section, are each sufficiently small to pass through a conventional trocar or other access port instrument into the abdomen.

In accordance with another preferred aspect of the intra-abdominal liver retraction device of this invention, the J or L shaped body is an integral unit.

In accordance with another preferred aspect of the intra-abdominal liver retraction device of this invention, the J or L shaped body comprises nylon or polycarbonate.

In accordance with another preferred aspect of the intra-abdominal liver retraction device of this invention, the stabilizing member includes a first opening located adjacent one of the pair of ends, and a second opening located adjacent another of the pair of ends, and wherein each of the openings is configured to be grasped by a grasping member to move the stabilizing member to the second orientation.

Another aspect of this invention is a method of lifting the liver of a patient having an abdomen, an abdominal wall and a diaphragm. The method comprises providing an intra-abdominal liver retraction device comprising a generally J or L shaped body, a stabilizing member, and a flexible filament. The generally L-shaped body includes an elongated section having at a proximal end and a distal end. The distal end forms a foot section extending at an angle to the elongated section. The stabilizing member has a pair of ends disposed opposite each other and is coupled to the proximal end and configured to be moved with respect thereto from a first orientation to a second orientation and vice versa. The stabilizing member when in the first orientation extends generally perpendicular to the elongated section. The stabilizing member when in second orientation extends generally parallel to the elongated section. The flexible filament is connected to the elongated section of the generally J or L shaped body between the foot section and the proximal end. The intra-abdominal liver retraction device with the stabilizing member orientated in the second orientation is introduced through a port in the abdominal wall into the abdomen. The stabilizing member is oriented in the first orientation when the intra-abdominal liver retraction device is within the abdomen. The foot section is brought to a position adjacent the diaphragm and with a portion of the elongated section and disposed under the liver and at least a portion of the foot section disposed under the liver. The flexible filament is drawn through an aperture in the abdominal wall from outside the abdomen to bring the stabilizing member into frictional engagement with a portion of the inner surface of the abdominal wall causing the elongated section and the foot section to lift the liver upward towards the abdominal wall.

In accordance with one preferred aspect of the method of this invention, the intra-abdominal liver retraction device is introduced through a small port into the abdomen by use of a trocar extending through the small port.

In accordance with another preferred aspect of the method of this invention, the generally J or L shaped body is somewhat flexible, yet self-supporting. The generally J or L shaped body is bent into a somewhat linear shape for insertion through the trocar into the abdomen.

In accordance with another preferred aspect of the method of this invention, the stabilizing member is swiveled to the second orientation from within the abdomen to enable the intra-abdominal liver retraction device to be withdrawn from the abdomen via a trocar.

In accordance with another preferred aspect of the method of this invention, the method additionally comprises grasping a portion of the stabilizing member by a grasping tool inserted through a trocar to swivel the stabilizing member to the second orientation and pulling the intra-abdominal liver retraction device out of the abdomen through the trocar.

In accordance with another preferred aspect of the method of this invention, the stabilizing member includes a first opening located adjacent one of the pair of ends, and a second opening located adjacent another of the pair of ends. One of the openings of the stabilizing member is grasped by the grasping tool to swivel the stabilizing member to the second orientation.

In accordance with another preferred aspect of the method of this invention, the method additionally comprises piercing the abdominal wall from outside thereof to form the aperture, introducing a grasping instrument through the aperture into the abdomen to grasp a portion of the flexible filament, and drawing the portion of the filament through the aperture to a position outside the abdominal wall.

In accordance with another preferred aspect of the method of this invention, the method additionally comprises releasably securing a clip to a portion of said filament outside the abdominal wall to maintain tension on said filament.

In accordance with another preferred aspect of the method of this invention the clip is released from the portion of the filament outside the abdominal wall thereby releasing tension in the filament and grasping a portion of the stabilizing member by a grasping tool to swivel the stabilizing member to the second orientation and pulling the device out of the abdomen through the trocar.

A further aspect of this invention is an another intra-abdominal liver retraction device for use in a patient. The patient has a liver, an abdominal cavity, an abdominal wall and a diaphragm. The intra-abdominal liver retraction device is configured to be introduced into the abdominal cavity via an instrument port extending through the abdominal wall during an insertion mode of operation. The intra-abdominal liver retraction device comprises a first section, a second section, a third section, and a flexible filament. The first and second sections are secured together at a first pivotable joint. The first section is configured to be flexed into a generally linear elongated shape during an insertion mode of operation. The first section has a distal end and a proximal end. The second section has a generally linear elongated shape. The third section has a generally linear shape and is pivotably connected to the second section by a second pivotable joint, whereupon the third section extends parallel to the second section. The second pivotable joint is releasable. The second and the third sections are configured to extend parallel to each other and substantially collinearly with the first section during the insertion mode of operation. The flexible filament has a distal end portion, an intermediate portion, and a proximal end portion. The distal end portion is secured to the distal end of the first section. The intermediate portion is located between the distal end portion and the proximal end portion and is configured to be pulled during a deployment mode of operation to cause the third section to pivot with respect to the second section at the second pivotable joint whereupon the second section and the third section extend at an angle to each other with a distal end of the third section being immediately adjacent the distal end of the first section, whereupon a portion of the first section and a portion of at least one of a distal end of the second section and the distal end of the third section form a liver support surface configured to be disposed under a portion of the liver to lift the liver during a lifting mode of operation.

In accordance with one preferred aspect of the other intra-abdominal liver retraction device of this invention, the intermediate portion of the filament extends out of an opening in the third section located between the distal end of the third section and a proximal end of the third section. The proximal end portion of the filament is configured to be extended through an aperture in the abdominal wall and pulled from outside the patient when the liver support surface is located under the liver to cause a proximal end of the third section to be in engagement with an inner surface portion of the abdominal wall and with the intermediate portion of the filament located between the liver support surface and the proximal end of the third section to lift the liver towards the abdominal wall during the lifting mode of operation.

In accordance with another preferred aspect of the other intra-abdominal liver retraction device of this invention, the intra-abdominal liver retraction device is configured to be removed from the abdomen during a removal mode of operation by grasping the distal end portion of the filament to pull the distal end of the first section into an instrument port extending into the abdominal cavity, whereupon the first section becomes linearized to pass into and through the instrument port followed by the second section, and thereafter followed by the third section which separates from the second section but is coupled to the second section by a portion of the filament so that the third section also passes through the instrument port.

In accordance with another preferred aspect of the other intra-abdominal liver retraction device of this invention, the first section has a generally Z or undulating shape.

In accordance with another preferred aspect of the other intra-abdominal liver retraction device of this invention, the position of the third section can be adjusted with respect to the second section.

In accordance with another preferred aspect of the other intra-abdominal liver retraction device of this invention, the second section additionally comprises a flexible projection configured to be grasped by a grasping instrument for adjustment of the position of the second and third sections with respect to each other.

In accordance with another preferred aspect of the other intra-abdominal liver retraction device of this invention, the second section is a top leg section and the third section is a bottom leg section disposed under the top leg section. The top leg section has a proximal end and a slot interposed between the distal end of the top leg section and the proximal end of the top leg section. The bottom leg section includes a distal opening at the distal end thereof, and an intermediate opening located between the distal opening of the bottom leg section and the proximal end of the bottom leg section. The intermediate opening of the bottom leg section intersects the slot of the top section at a movable intersection. The filament extends through the distal opening in the bottom leg section.

In accordance with another preferred aspect of the other intra-abdominal liver retraction device of this invention, the filament includes a portion extending through the movable intersection to form the second pivotable joint and wherein the position of the third section can be adjusted with respect to the second section at the second pivotable joint.

In accordance with another preferred aspect of the other intra-abdominal liver retraction device of this invention, the proximal end portion of the filament is bulbous and wherein the slot includes an enlarged opening adjacent a proximal end of the slot. The enlarged opening is of a sufficient size to permit the bulbous proximal end portion of the filament to pass therethrough to enable the bottom leg section to separate from the top leg section and to trail the top leg section through the instrument port.

In accordance with another preferred aspect of the other intra-abdominal liver retraction device of this invention, the intra-abdominal liver retraction device additionally comprises a ring of flexible material extending about contiguous portions of the top leg section and the bottom leg section slightly proximally of second pivotable joint to hold the contiguous portions together during the insertion, deployment and lifting modes of operation.

In accordance with another preferred aspect of the other intra-abdominal liver retraction device of this invention, the ring of flexible material is trapped to the bottom leg section by a portion of the filament extending through the distal opening of the bottom leg section and through the intermediate opening in the bottom leg section after the bottom leg section has been separated from the top leg section, whereupon the ring of flexible material is removed from the abdomen with the removal of the intra-abdominal liver retraction device from the abdomen during the removal mode of operation.

In accordance with another preferred aspect of the other intra-abdominal liver retraction device of this invention, the distal end portion of the filament extends through an opening in the distal end of the top leg section to form a grasping portion configured to be grasped by a grasping instrument to pull the distal end of the first section into the instrument port.

A further aspect of this invention is a another method of lifting the liver of a patient having an abdomen, an abdominal wall and a diaphragm. The method comprises providing an intra-abdominal liver retraction device comprising a first section, a second section, a third section and a flexible filament. The first and second sections are secured together at a first pivotable joint. The first section has a distal end and a proximal end. The second section has a generally linear elongated shape. The third section has a generally linear shape and is pivotably connected to the second section by a second pivotable joint, whereupon the third section extends parallel to the second section. The second pivotable joint is releasable. The second and the third sections are configured to extend parallel to each other. The flexible filament couples the first, second and third sections together and has a distal end portion and a proximal end portion. The distal end portion is secured to the distal end of the first section. The second and third sections are substantially parallel to each other. The first member is pivoted about the first pivotable joint so that the second and third sections are substantially collinear with the first section. The first section is introduced through an instrument port extending through the abdominal wall into the abdominal cavity during an insertion mode of operation to cause the first to readily pass through the instrument port followed by the second and third sections. Portions of the intra-abdominal liver retraction device are grasped and the proximal end portion of the filament is pulled during a deployment mode of operation to cause the third section to pivot with respect to the second section at the second pivotable joint whereupon the second section and the third section extend at an angle to each other with a distal end of the third section immediately adjacent to the distal end of the first section and with a portion of the first section and a portion of at least one of a distal end of the second section and the distal end of the third section forming a liver support surface. At least a portion of the liver support surface is disposed under a portion of the liver to lift the liver during a lifting mode of operation.

In accordance with one preferred aspect of the other method of this invention, the proximal portion of the filament is drawn through an aperture in the abdominal wall from outside the patient so that a portion of the filament is located outside of the patient wherein the filament brings the proximal end of the third section into engagement with an inner surface portion of the abdominal wall, with the intermediate portion of the filament located between the liver support surface and the proximal end of the third section to thereby lift the liver towards the abdominal wall to an elevated position during the lifting mode of operation In accordance with another preferred aspect of the other method of this invention, the method additionally comprises holding the proximal portion of the filament that is located outside the patient in place to hold the liver at the elevated position.

In accordance with another preferred aspect of the other method of this invention, the method additionally comprises releasing the proximal portion of the filament that is located outside the patient to lower the liver from the elevated position to a lowered position.

In accordance with another preferred aspect of the other method of this invention, the method additionally comprises removing the intra-abdominal liver retraction device from the abdominal cavity of the patient during a removal mode of operation.

In accordance with another preferred aspect of the other method of this invention, the removal mode of operation is accomplished by grasping the distal end portion of the filament to pull the distal end of the first section into an instrument port extending into the abdominal cavity, whereupon the first section passes into and through the instrument port followed by the second section, and thereafter followed by the third section which separates from the second section but is coupled to the second section by a portion of the filament so that the third section also passes through the instrument port.

In accordance with another preferred aspect of the other method of this invention, the first section comprises a generally Z or undulating shaped member which is configured to be linearized when passing through the instrument port during the insertion mode of operation and during the removal mode of operation.

In accordance with another preferred aspect of the other method of this invention, the instrument port comprises a 12 mm trocar.

BRIEF DESCRIPTION OF THE DRAWING FIGURES

FIG. 3 is another isometric view of the exemplary embodiment of the intra-abdominal liver retraction device shown in FIGS. 1 and 2;

FIG. 4 is a top plan view of the exemplary embodiment of the intra-abdominal liver retraction device shown in FIGS. 1-3;

FIG. 5 is a bottom plan view of the exemplary embodiment of the intra-abdominal liver retraction device shown in FIGS. 1-3;

FIG. 9 is an illustration in the form of a cross sectional view of the abdominal wall and abdominal cavity in the abdomen of a patient whose liver is shown supported by an exemplary embodiment of an intra-abdominal liver retraction device constructed in accordance with this invention shown during a lifting mode of operation in accordance with a method of this invention;

FIG. 10 is an illustration in the form of a top plan view of the exemplary instrument shown in FIG. 1 supporting the patient's liver thereon during the lifting mode of operation;

FIG. 11 is a reduced isometric view of the exemplary intra-abdominal liver retraction device of FIG. 9 shown ready to be inserted through a conventional trocar into the abdominal cavity of a patient during an insertion mode of operation in accordance with a method of this invention;

FIG. 12 is a slightly enlarged side elevational view of the exemplary intra-abdominal liver retraction device shown FIG. 11;

FIG. 13 is an enlarged exploded isometric view of the components making up the exemplary intra-abdominal liver retraction device shown in FIGS. 9-12;

FIG. 14 is an enlarged isometric view of a generally Z or undulating shaped component forming a first section of the intra-abdominal liver retraction device, shown in FIGS. 9-13;

FIG. 15 is an enlarged isometric view of a top leg section component forming a second section of the intra-abdominal liver retraction device, shown in FIGS. 9-13;

FIG. 15A is an end view taken along line 15A-15A in FIG. 15;

FIG. 16 is an enlarged isometric view of a bottom leg section component forming a third section of the intra-abdominal liver retraction device, shown in FIGS. 9-13;

FIG. 17 is an enlarged isometric view of the bottom leg section of the intra-abdominal liver retraction device, shown in FIG. 16 but taken from the opposite side thereof;

FIG. 18 is an enlarged isometric view of an O-ring component of the intra-abdominal liver retraction device, shown in FIGS. 9-13;

FIG. 19 is an enlarged isometric view of a rivet component of the intra-abdominal liver retraction device, shown in FIGS. 9-13;

FIG. 20 is an enlarged isometric view of the exemplary intra-abdominal liver retraction device shown in FIGS. 9-13 shown in a configuration into which it is placed during a deployment mode of operation in accordance with a method of this invention;

FIG. 21 is a top plan view of the exemplary intra-abdominal liver retraction device of FIGS. 9-13 shown after it has been removed from the body of the patient through a trocar during a removal mode of operation in accordance with a method of this invention; and FIG. 22 is a bottom plan view of the exemplary intra-abdominal liver retraction device shown in FIGS. 9-13 after it has been removed from the body of the patient through a trocar during a removal mode of operation in accordance with a method of this invention.

DETAILED DESCRIPTION OF THE PREFERRED EMBODIMENTS OF THE INVENTION

Figure 1:
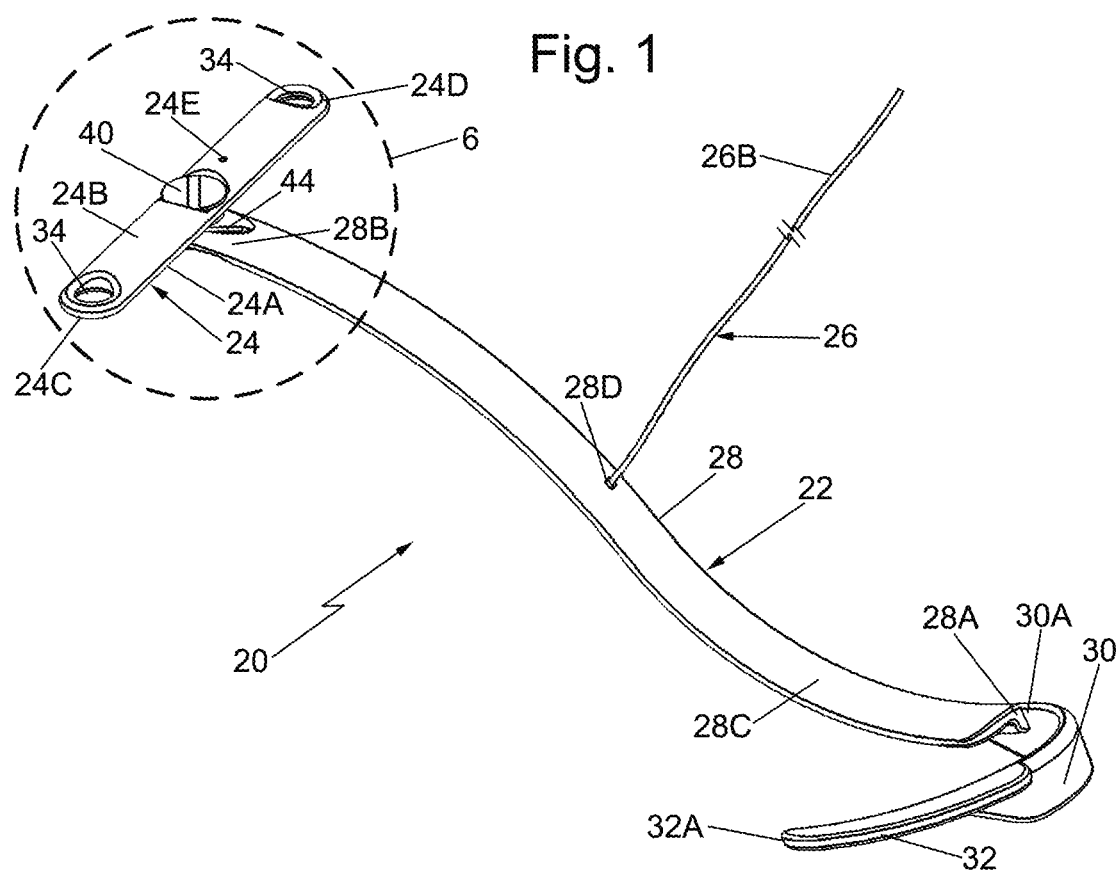
FIG. 1 is an isometric view of one exemplary embodiment of an intra-abdominal liver retraction device constructed in accordance with this invention.
Figure 8:
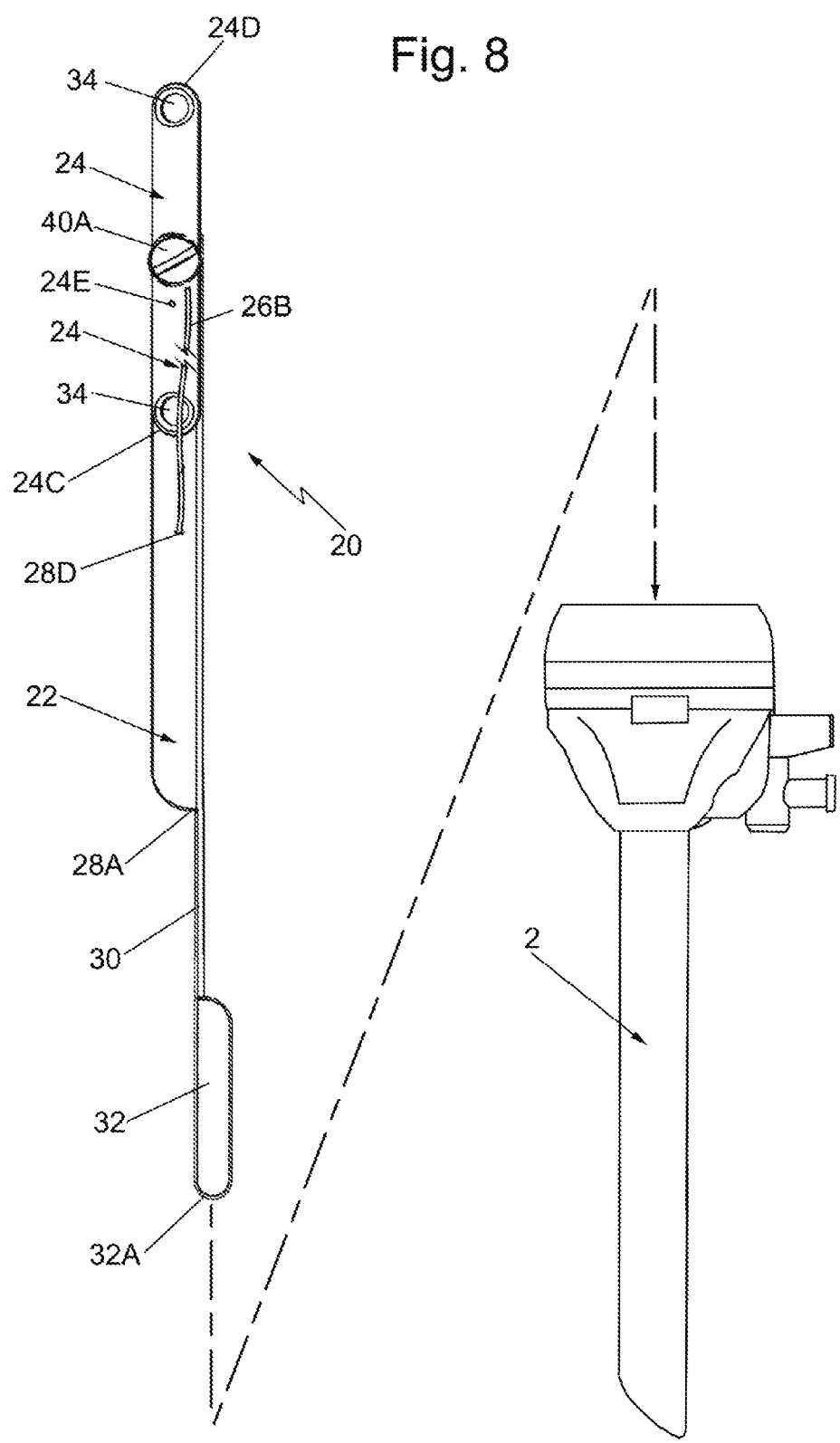
FIG. 8 is an illustration of the exemplary embodiment of the intra-abdominal liver retraction device of FIGS. 1-7 shown in a linearized state it will assume as it is introduced through a conventional trocar to carry out the laparoscopic procedure shown in FIG. 2.

Referring now to the various figures of the drawing wherein like reference characters refer to like parts, there is shown in FIG. 1 an exemplary intra-abdominal liver retraction device 20 constructed in accordance with this invention. As will be described in detail later, the device 20 is configured to be collapsed and linearized so that it can be readily introduced through a conventional trocar 2 (FIG. 8) or some other access port instrument through the patient's abdominal wall 4 (FIG. 2) into the patient's abdominal cavity 6, and thereafter opened so that the patient's liver 8 can be disposed on a portion of it for lifting or otherwise retracting to provide access to some other anatomical structure, e.g., the stomach 10 for some laparoscopic bariatric procedure, in the abdominal cavity.

The intra-abdominal liver retraction device 20 basically comprises an assembly of a body 22, a stabilizing member 24, and a lifting or elevating filament 26. The body 22 is of a general J-shape when viewed from above or below (FIGS. 4 and 5, respectively). The generally J-shaped body 22 preferably is an integral member and includes an elongated section 28, an intermediate section 30 and a foot section 32. The elongated section 28 has a distal end 28A and a proximal end 28B. The distal end 28A terminates at one end 30A of the intermediate section 30. The opposite end 30B of the intermediate section 30 terminates at the foot section 32 (FIG. 5). The intermediate section, when viewed from above or below is of a general V-shape and serves as a hinge between the elongated section 28 and the foot section 32. The foot section 32 is an elongated member when viewed from above or below and terminates in a distal end 32A.— When viewed from the side the foot section 32 is slightly concave. The slight concavity of the foot section enables the foot section to safely accommodate a portion of the liver 8 thereon when the device 20 is used, as will be described later. The elongated section 28 when viewed from the side is in the form of a generally S-shaped curve, whose distal end portion 28C is concave to safely accommodate another portion of the liver thereon. Nevertheless, being elongated the section 28 has a longitudinal axis LA as best seen in FIG. 4. The elongated and slightly concave foot section 32 extends at an acute angle, e.g., approximately sixty degrees, to the longitudinal axis LA of elongated section 28 when viewed from above or below. If desired, the angle of the foot section to the longitudinal axis LA could be approximately ninety degrees. In such a case the body 22 will be generally L-shaped instead of generally J-shaped.

In any case the body 22 is formed of somewhat flexible, yet self-supporting material, e.g., nylon, polycarbonate, or other similar materials, so that it can be bent from its normal shape, like shown in FIG. 1, into a straightened or linearized configuration along the longitudinal axis LA. This action is necessary to enable the intra-abdominal liver retraction device 20 to be inserted into the trocar 2 or any other instrument port extending into the abdomen 12 of the patient like shown in FIG. 8, so that the device 20 is located in the abdominal cavity 6 like shown in FIG. 2. Once inside the abdominal cavity and free of the trocar the device will automatically reassume its normal shape. In particular, the generally S-shaped elongated section 28 is designed to be bent so that when viewed from the side it is linear instead of being S-shaped. Similarly, the hinge section 30 can be bent so that when viewed from above or below it is linear instead of being of a V-shaped.

As will be described later the stabilizing member 24 is configured to be naturally biased by biasing means into a first orientation wherein its long dimension extends generally perpendicularly to the longitudinal axis LA. The stabilizing member is also configured so that it can be moved, e.g., swiveled, into a second orientation against force provided by the biasing means, so that its long dimension extends generally parallel to the longitudinal axis LA like that shown in FIG. 8. In this state the intra-abdominal liver retraction device 20 can be introduced into the abdomen of the patient through the trocar 2. Once in the abdominal cavity and free of the trocar the stabilizing member 24 will automatically assume its first configuration, i.e., extend perpendicularly to the longitudinal axis LA, by the force provided by the biasing means and the curved portions of the body will reassume their naturally curved shape.

As will be described later the foot section 32 is configured to be located adjacent the patient's diaphragm 12 when the device 20 is used to elevate the patient's liver 8. Thus, the foot section 32 need not be anchored to the diaphragm 12, as is the case with prior art devices. Instead, it is the stabilizing member 24 in cooperation with the lifting or elevating filament 26 which holds the device 20 in position elevating the liver during use.

The elevating or lifting filament 26 is formed of any suitable material, e.g., nylon braided suture, and is relatively long, e.g., approximately 12 inches. One end of the filament 26 is extended through a small aperture 28D (FIGS. 1 and 4) in a midportion of the elongated section 28 and is secured thereto by a knot 26A. The opposite end portion 26B of the filament 26 is free and is configured to be carried from inside the abdominal cavity through a small aperture 4A (FIG. 2) in the abdominal wall 4 to a position outside the abdominal wall where it is releasably locked in place by a clip 14, as will be described later.

Figure 6:
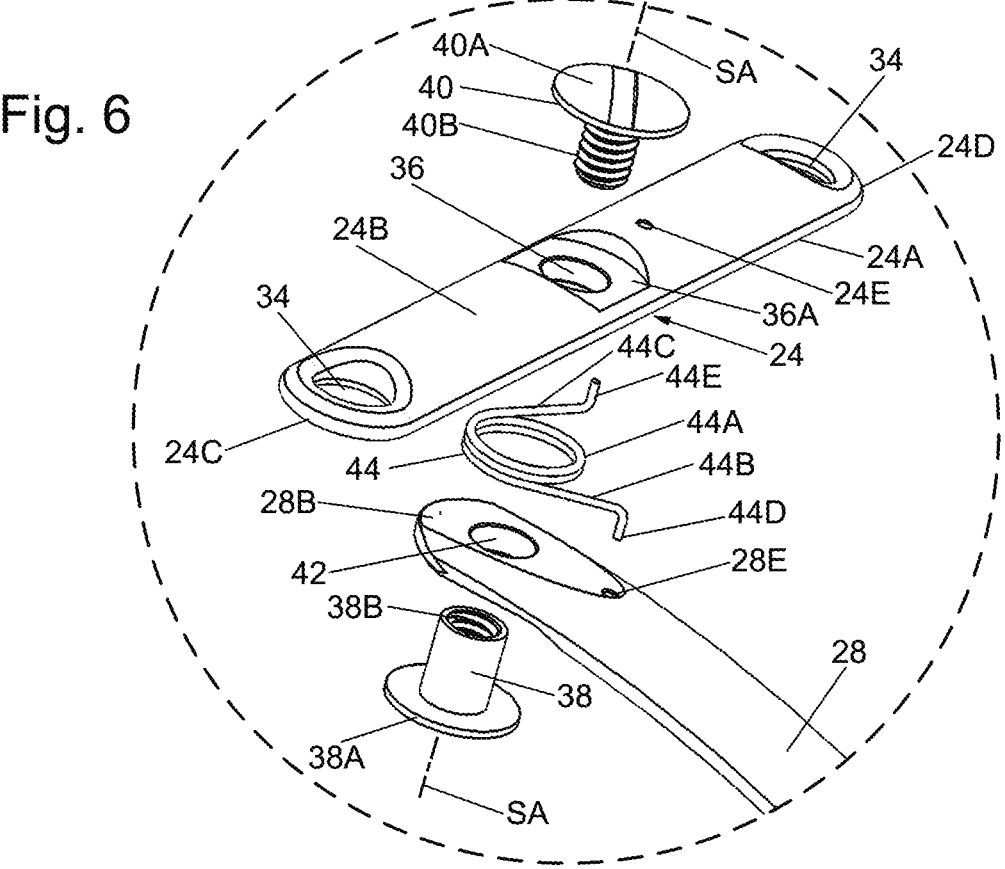
FIG. 6 is an exploded isometric view of the components of the exemplary embodiment of the intra-abdominal liver retraction device shown within the broken circle designated by the reference number 6 in FIG. 1.
Figure 7:
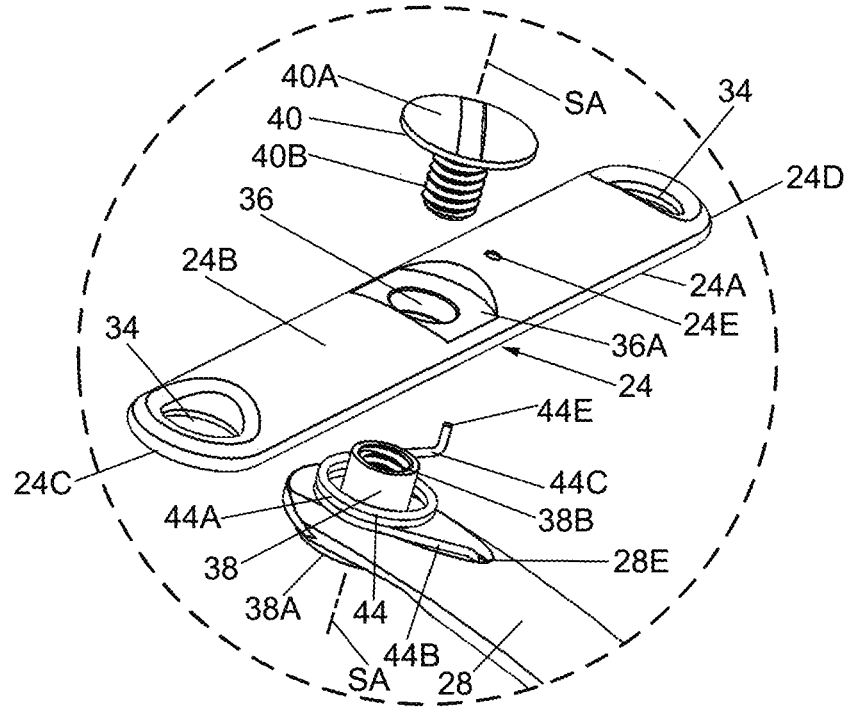
FIG. 7 is a partially exploded isometric view of the components of the exemplary embodiment of the intra-abdominal liver retraction device shown in FIG. 6.

The stabilizing member 24 basically comprises an elongated bar, preferably formed of the same material as that making up the body 22. The bar has a planar undersurface 24A and a convex upper surface 24B and includes a pair of ends 24C and 24D, each of which includes a respective opening 34 thereat. Each opening 34 is chamfered where it merges with the upper surface 24B. A central opening or hole 36 (FIGS. 6 and 7) is located midway between the ends 24C and 24D of the stabilizing member to accommodate a swivel assembly (to be described shortly). The swivel assembly enables the stabilizing member 24 to be swiveled or rotated into either of the first or second orientations mentioned above. The swivel assembly is best seen in FIGS. 6 and 7 and basically comprises an internally threaded hub 38 and an externally threaded screw 40. The hub includes a head 38A and an internally threaded socket 38B. The socket is extended through a hole 42 at the proximal end 28B of the elongated member 28 such that the head 38A of the hub is located under the elongated member, with the threaded socketed 38B facing upward. The screw 40 includes a slotted head 40A and an externally threaded shank 40B. The threaded shank 40B of the screw is inserted along axis SA (FIGS. 6 and 7) through the hole 36 in the stabilizing member so that its external threads threadedly engage the internal threads of the socket 38B, and with the head 40A of the screw being located within a recess 36A surrounding the opening 36 in the stabilizing member. The axis SA forms what can be referred to as the "swivel" axis and is the axis about which the stabilizing member 24 is pivoted or swiveled between its first and second orientations and vice versa.

As mentioned earlier the stabilizing member is naturally biased by biasing means to be in the first orientation like shown in FIG. 1. That biasing means can take various forms. In the exemplary embodiment of FIG. 1, the biasing means is in the form of a helical spring 44. That spring includes a central coil 44A through which the socket 38B of the hub 38 extends (best seen in FIG. 7) and a pair of extending linear leg portions 44B and 44C. The swivel axis SA extends through the center of the coil, with the leg portions 44B and 44C extending perpendicularly to each other and perpendicularly to the swivel axis. The leg portions 44B and 44C terminate in tab portions 44D and 44E, respectively. Each of the tab portions extends parallel to the swivel axis SA. As best seen in FIG. 6, the tab portion 44E is configured to be located within a small aperture 24E in the stabilizing member 24 to secure the leg portion 44C of the spring thereto. The other tab portion 44D is configured to be located within a small aperture 28E in the elongated member 28 to secure the leg portion 44B of the spring thereto. With the perpendicularly extending leg portions of the spring secured to the stabilizing member and the elongated section as just described, the spring in its natural or unbiased state will hold the stabilizing member so that its long axis is perpendicular to the longitudinal axis LA of the body 22 (i.e., the stabilizing bar will be in the first orientation). Pulling or pushing on either end of the stabilizing member in either the clockwise or counter-clockwise direction will cause the stabilizing member to pivot or swivel about the swivel axis SA against the bias provided by the spring 44.

Figure 2:
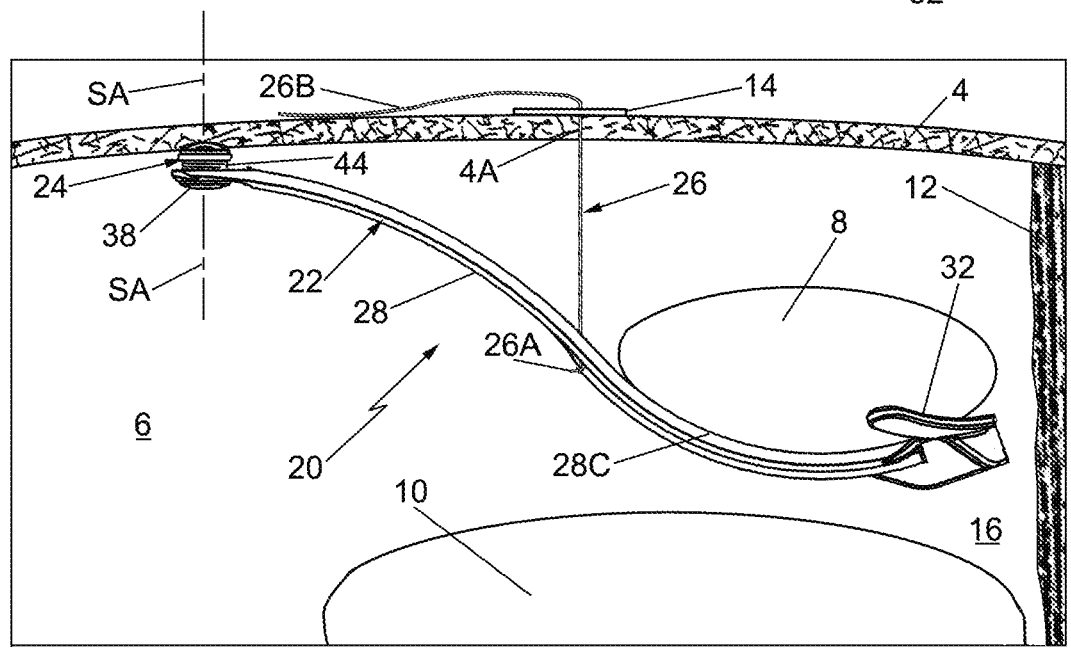
FIG. 2 is an illustration of the use of the intra-abdominal liver retraction device of FIG. 1 shown in use in accordance with a method aspect of this invention to elevate the liver of a patient in the patient's abdomen during a laparoscopic procedure, e.g., a bariatric procedure.

Use of the exemplary intra-abdominal liver retraction device 20 (or any other device constructed in accordance with this invention) to elevate the liver of a patient will now be described with reference to FIG. 2. In particular, a conventional trocar 2 or some other access port is introduced into the patient's insufflated abdominal cavity 6 where the laparoscopic procedure is to be carried out. The stabilizing member 24 of the intra-abdominal liver retraction device 20 is manually rotated or swiveled about the axis SA until its long dimension is parallel to the longitudinal axis LA. The distal end 32A of the foot section is then introduced into the trocar and the intra-abdominal liver retraction device 20 pushed in. That action will straighten or linearize the body 22 as it passes through the trocar until the entire device is within the abdominal cavity. If necessary a grasper (not shown) extending through another trocar (not shown) or other instrument port into the abdominal cavity can be used to pull the device 20 fully into the abdominal cavity.

Once the device 20 is fully within the abdominal cavity the stabilizing member 24 will be free, whereupon the natural biasing force applied by the spring will cause the stabilizing member to swivel or rotate back to the first orientation, like shown in FIG. 1. Once the device is in that state, a grasper (not shown) extending through the introducing trocar can be used to grasp the foot section 28 to carry it to a position adjacent the patient's diaphragm and under a portion of the patient's liver so that the distal portion 28C of the elongated member 28 is under a contiguous portion of the patient's liver.

After that has been accomplished a conventional needle-driver (not shown) or some other piercing instrument can be used to pierce the abdominal wall 4 from the outside to create the small aperture 4A in the abdominal wall. It is through that aperture that the free end portion 26B of the lifting filament 26 will be drawn from inside the abdominal cavity to a position outside the abdominal cavity. If the needle which makes the aperture 4A includes some type of grasping feature it can be used to grasp the free end portion 26B and carry it from inside the abdominal cavity to outside the abdominal cavity through the aperture 4A. If that needle doesn't include any such grasping feature another instrument having a grasping feature can be introduced through the aperture 4A into the abdominal cavity to grasp the free end portion 26B of the filament and carry it out through the aperture to outside the abdominal wall. The portion of the lifting filament outside of the abdominal cavity is then retracted or pulled to pull the device 20 toward the inner surface of the abdominal wall. This action is continued until the stabilizing member 24 frictionally engages the inner surface of the abdominal wall. Once that has occurred continued pulling on the lifting filament will result in the device 20 operating like a cantilever beam, with the stabilizing member frictionally engaging the inner surface of the abdominal wall along a line extending perpendicularly to the longitudinal axis LA. The opposite (distal) end of the device 20 will then be pivoted upward (counterclockwise in FIG. 2) whereupon its foot section 32 and the portion 28C of its elongated section 28 will lift the liver from its normal position to a desired elevated position, thereby exposing the stomach 10. When the liver is at the desired elevated position a conventional surgical clamp or clip, such as a hemostat 14 (or some other securement device), is used to releasably secure the filament portion 26B to the outside of the abdominal wall 4. This action maintains tension on the lifting filament 26 and thus holds the liver at the elevated position.

As should be appreciated by those skilled in the art since the distal portion of the elongated section 28C curves upward, as does foot section, there will be significant room or space 16 below the foot section and above the stomach to enable the surgeon to visualize the stomach without interference from the device 20. The surgeon can thus perform whatever procedure is desired on the stomach while the liver is held in the elevated position so that it does not interfere with the procedure.

Once the laparoscopic procedure has been completed and it is desired to relocate the liver to its normal position and remove the device 20 from the abdominal cavity all that is required is to remove the clip 14, thereby freeing the portion 26B of the lifting filament. The freed lifting filament portion 26B can then be pulled back through the aperture 4A into the abdominal cavity by means of a grasper (not shown) extending through a trocar into the abdominal cavity. The foot section 32 can then be pulled out from below the liver by that grasper or another grasper. That grasper can then be used to swivel or pivot the stabilizing member to its second orientation wherein the stabilizing member extends parallel to the longitudinal axis LA. In particular, the grasper is manipulated to grasp one of the openings 34 of the stabilizing member. The opening 34 provide a good engagement point to be grasped by the jaws of the grasper to swivel the stabilizing member with respect to the elongated section against the bias of the spring 44 so that the stabilizing member is in its second orientation. Once the stabilizing member is in that orientation it can be pulled by that grasper into the distal end of the trocar through which the grasper extends. The device 20 can then be pulled by that grasper to cause more of the device 20 to enter into the trocar from within the abdominal cavity. As each portion of the device is pulled into the trocar it will bend to straighten itself to enable it to pass through the trocar until the entire device is fully out of the patient.

It should be appreciated by those skilled in the art, that while the intra-abdominal liver retraction device 20 of the subject invention has particular utility for retracting the liver of a patient, the device is not limited to use with that particular organ. Thus, devices constructed in accordance with this invention and their method of used can be used to elevate or retract other organs or anatomic structures within the body of a patient during a laparoscopic procedure. Further still, various changes can be made to the structure of the device and its methods of use, other than those specifically described or disclosed above.

In the interest of facilitating the visibility of structures within the abdominal cavity, the intra-abdominal liver retraction device may be formed of a translucent material to enable light to shine therethrough, so that it will not obscure or otherwise interfere with the field of view of the surgeon performing the laparoscopic procedure.

One exemplary embodiment of the intra-abdominal liver retraction device of this invention can have the following dimensions. When the body 22 is straightened or linearized like shown in FIG. 8, the elongated section 28 is approximately 6.10 inches in length, the foot section 32 is approximately 1.83 inches in length, and the intermediate section is approximately 1.26 inches in length. The stabilizing member is approximately 3.0 inches in length. When the stabilizing member is in the second position like shown in FIG. 8 the overall length of the device 20 is approximately 10.4 inches. The maximum width of the stabilizing member and the elongated section 28 of the body is approximately 0.48 inch. The maximum width of the foot section 32 is approximately 0.42 inch. Thus the device 20 can be passed through the passageway of a conventional trocar. All of those dimensions are merely exemplary and thus the device 20 can be of different dimensions, if desired. Moreover, other changes to the device 20 are contemplated within the scope of this invention, so that the subject invention should not be deemed limited to the features of the exemplary device 20 described above.

It should be point out at this juncture that the device and method as described above may in some cases leaves something to be desired from the standpoint of the effectiveness of the lifting or retraction of the liver to provide adequate visualization of the hiatus. To address that drawback, that end, the subject invention also includes another device and method which will be discussed immediately below and which are shown in FIGS. 9-22.

FIG. 9 is an alternative exemplary intra-abdominal liver retraction device 120 constructed in accordance with this invention. As will be described in detail later, the device 120 is configured to be collapsed and linearized, like shown in FIG. 11, so that it can be readily introduced through a conventional trocar 2, e.g., a 12 mm trocar, or some other access port instrument through the patient's abdominal wall 4 into the patient's abdominal space or cavity 6, adjacent the patient's diaphragm 18 and thereafter opened. Once opened, it can be manipulated by graspers or other instruments extending into the abdominal cavity so that the patient's liver 8 is, disposed on a portion of it, whereupon the liver can be lifted or otherwise retracted for some medical purpose like shown in FIGS. 9 and 10. One exemplary purpose is to provide access to some other anatomical structure, e.g., the underlying stomach 10, in a laparoscopic bariatric procedure.

As will be described in detail later, the device 120 is arranged to be used in accordance with a method of this invention. That method basically entails several modes of operation, which are accomplished in sequence. In particular, during what can be termed an insertion mode of operation, the device is introduced into the abdominal cavity via the trocar or other instrument port. Once within the abdominal cavity the device can be manipulated during what can be termed a deployment mode of operation to configure it for disposition under the liver of the patient. Once properly positioned the device can be manipulated during what can be termed a lifting mode of operation to lift or otherwise retract the liver toward the abdominal wall so that the medical procedure can be accomplished. After that has occurred the device can be manipulated during what can be termed a removal mode of operation to remove it as a unit from the patient's abdominal cavity.

The exemplary intra-abdominal liver retraction device 120 is best seen in FIGS. 11, 13 and 20 and basically comprises an assembly of a first section 122, a second section 124, a third section 126, a flexible filament 128, an O-ring 130 and a rivet 132.

As best seen in FIGS. 13 and 14 the first section 122 is a somewhat elongated integral member including sequentially located portions 122A, 122B, 122C, 122D, and 122E, which when viewed from above or below form a generally Z or undulating shaped member. The portions 122A, 122C and 122E are generally planar horizontal strips when viewed from the side and are interconnected by the portions 122B and 122D, respectively. In particular, the section 122B is in the form of a downwardly extending flange that forms a flexible joint between the portions 122A and 122C. In a similar manner, the section 122D is in the form of a downwardly extending flange that forms a flexible joint between the portions 122C and 122E. The top surface 138 of the portions 122A, 122C and 122E are flat and coplanar. The first section 122 has a distal end 134 (located at the distal end of the section 122A) and a proximal end 136 (located at the proximal end of the section 122E). A distal opening or hole 140 is located at the distal end 134 of the first section 122. A proximal opening or hole 142 is located at the proximal end 136 of the first section 122.

The first section 122 is formed as an integral unit of a biocompatible strong plastic material, e.g., Nylon, with the flange portions 122B and 122C being capable of being bent or flexed to bring the portions 122A, 122C and 122E from their normal generally Z or undulating configuration into a more linear alignment so that the first section can be linearized to pass through the lumen of the trocar during the insertion mode of operation (to be described in detail later). Once introduced into the abdominal cavity and free of the trocar, the first section will return or spring back to its normal generally Z or undulating shape.

The second section 124 of the device 120 is best seen in FIGS. 13 and 15 and forms what can be called a top leg section. The top leg section 124 is an elongated member that is generally linear in shape, although it curves slightly when viewed from either side. The top leg section includes a distal end 144 and a proximal end 146. The lower or undersurface 148 of the second section is flat when viewed in transverse cross section, with the upper surface 150 of the second section arcuate when viewed in transverse cross section. The distal end 144 of the second section includes a ledge 152 that is configured to receive the proximal end of the first section at a first pivotable joint. To that end a distal opening or hole 154 is located in the ledge. The opening 154 is configured to be axially aligned with the proximal opening or hole 142 in the proximal end of the first section and with the rivet 132 located within those axially aligned openings to pivotably connect the two sections together.

The top leg section also includes an elongated keyhole shaped slot 156 extending along a substantial length thereof from approximately the middle of the section to a point adjacent the proximal end 146 of the section. The slot 156 extends through the top leg section from the lower surface 148 to the upper surface 150 and is chamfered at the upper surface. The end of the slot 156 located closest to the proximal end 146 of the top leg section includes an enlarged opening 158.

As best seen in FIGS. 15 and 15A a pair of openings or holes 160 extends through the portion of the top leg section adjacent the ledge 152 from the bottom surface 148 to the top surface 150. The openings or holes 160 are chamfered at the top surface 150. A short section of a flexible filament extends through the pair of holes to form a flexible projecting loop 162 at the underside of the top leg section. Each end of the filament section is knotted, with the knots being disposed and secured in the respective chamfered portions of the pair of openings 160 to secure the filament loop 162 in place. As will be described later the filament loop 162 is configured to be grasped by any conventional grasping instrument when the device 120 is located within the abdominal cavity to position and orient the device 120.

The third section 126 of the device 120 is best seen in FIGS. 13, 16 and 17 and forms what can be called a bottom leg section. The bottom leg section 126 is an elongated member that is generally linear in shape, although it curves slightly when viewed from either side and is slightly longer in length than the top leg section 124. The upper surface 164 of the bottom leg section is flat when viewed in transverse cross section, with the lower or undersurface 166 being arcuate when viewed in transverse cross section. The bottom leg section includes a distal end 168 and a proximal end 170, with a distal opening or hole 172 being located in the distal end. The opening 172 extends from the upper surface 164 to the lower surface 166. The bottom leg section also includes an intermediate opening 174 located approximately in the middle of that section between its distal and proximal ends. The intermediate opening extends from the lower surface 166 to the upper surface 164 and is chamfered at each end.

As clearly shown in FIGS. 11 and 12 the top leg section 124 is disposed on top the bottom leg section 126, with the undersurface 148 of the top leg section abutting the top surface 164 so that their respective longitudinal axes are generally parallel to each other with the proximal end portion of the bottom leg member extending beyond the proximal end of the top leg section. The flexible loop 162 is flattened between the upper leg section and the bottom leg section when they are superimposed. As best seen in FIG. 16, the proximal end 170 of the bottom leg section 126 extends at a slight angle to the remainder of that section. As will be described later the upper surface 164 at the proximal end of the top leg section is configured to be brought into engagement with a portion of the undersurface of the patient's abdominal wall during a lifting mode of operation of the device 120.

The first, second and third sections of the device 120 are coupled together by the flexible filament 128. That filament is formed of any biocompatible material, e.g., size nine polyester suture material. The distal end portion of the filament extends through the distal opening 140 in the first section 122. The filament 128 is knotted on both sides of the opening 140 so that it is fixedly secured to the distal end of the first section, with an extension or tassel 176 of the filament projecting away from the distal end of the first section. The tassel 176 serves as a means for grasping the distal end of the device 120 to manipulate it as necessary during use, as will be described later. In accordance with a preferred embodiment of the invention the free end of the tassel is knotted or otherwise bulbous. The portion of the filament 128 located proximally of the distal opening 140 in the first section 122 extends under the first section and enters into the distal opening 172 of the bottom leg section 126 from the upper-side 164 thereof, from whence it passes along the underside 166 of the bottom leg section 126 to the intermediate opening 174 in the bottom leg section. The filament then passes through that opening and enters and passes through the slot 156 in the top leg section from the underside 148 of the top leg section. The remainder of the filament 128 to its proximal end is free, with the proximal end of the filament being either knotted or otherwise bulbous to form an enlarged free end 178.

The portion of the filament that passes through the intermediate opening 174 in the bottom leg section and through the slot 156 in the top section forms a second pivotable joint of the device 120. As will be described later the second pivotable joint is releasable to release during a portion of the removal mode of operation.

The O-ring 130 is formed of any suitable resilient material, e.g., nitrile, and is disposed about the top leg section 124 and bottom leg section 126 located just proximally of the second pivotable joint and serves to hold the top and bottom leg sections together during the insertion, deployment and lifting modes of operation of the device 120, but is configured to release from the top leg section to enable the bottom leg section to separate from the top leg section during a portion of the removal mode of operation, as will also be described later.

As mentioned earlier the top leg section 124 is disposed on the bottom leg section 126 and oriented so that their longitudinal axes are parallel to each other when the device 120 is configured for insertion into the abdomen of the patient during the insertion mode of operation. Both leg sections 124 and 126 are preferably formed of the same material as the first section 122 so that they can flex slightly to pass through the lumen of the trocar into the abdominal cavity and once inside return or spring back to their normal shape.

Turning now to FIGS. 9-11 and 20-22, one exemplary method of lifting the liver 8 of a patient will now be described. The method basically comprises providing an intra-abdominal liver retraction device 120 like that described above and configuring it into a somewhat linear configuration so that it can be introduced through the trocar 2 through the patient's abdominal wall 4 into the patient's insufflated abdominal cavity 6 during the insertion mode of operation. In particular, the top leg section 124 and the bottom leg section 126 are oriented so that their respective longitudinal axes are parallel to each other, with the top leg section disposed over the bottom leg section, and with the O-ring 130 disposed about those sections at a location distally of the intermediate opening 174 in the bottom leg section. The generally Z or undulating shaped first section 122 is pivoted about the axis of the first pivotable joint with respect to the top leg section 124 so that the top and bottom leg sections are substantially collinear with the first section like shown in FIG. 11. The distal end 134 of the first section 122 is juxtaposed with the trocar so that it is axially aligned along the longitudinal axis X extending through the lumen of the trocar. The distal end of the first section is then pushed through that lumen from outside the body of the patient until the distal end is within the insufflated abdominal cavity. The generally Z or undulating shaped first section will bend or flex into a generally linearized configuration as it is introduced through the lumen of the trocar. When the distal end of the first section 122 is within the insufflated abdomen the knotted tassel extension 176 at the distal end of the first section can then be grasped by the jaws of a conventional grasping device (not shown) that is introduced into the abdomen of the patient via some other instrument port. Once the tassel extension 176 has been grasped the device 120 can be pulled through the trocar's lumen so that the generally Z or undulating shaped first section is free of the trocar and entirely within the insufflated abdominal cavity. Once the first section is in the abdominal cavity and free of the trocar it will automatically assume its normal Z or undulating shape. The remainder of the device 120 can then be pulled into the abdominal cavity by that grasper by grasping the tassel extension 176 and/or by grasping the filament loop 162 adjacent the distal end of the top leg section 124.

Once the entire device 120 is within the abdominal cavity it is ready to be deployed into a position where it is ready to lift the liver 8 during the deployment mode of operation. That deployment mode of operation is as follows. As discussed previously the second pivotable joint is formed by the portion of the filament 128 extending through the intermediate opening 174 of the bottom leg section 124 and through the contiguous portion of the slot 156 of the top leg section 126. Any intermediate portion of the filament 128 extending proximally of the second pivotable joint can be grasped by a grasper (not shown) extended into the insufflated abdominal cavity. At the same time another grasper extended into the insufflated abdominal cavity can be used to grasp or otherwise hold a portion of the device 120 (e.g., the top leg section adjacent the second pivotable joint) stationary. The grasped intermediate portion of the filament 128 can then be pulled or drawn while holding the grasped portion of the top leg section 124 stationary, to cause the bottom leg section 126 to pivot about the second pivotable joint so that the top leg section and bottom leg section extend at an angle to each other. The drawing or pulling of the filament 128 to pivot the top leg section and bottom leg section with respect to each other also has the effect of bringing the distal end 168 of the bottom leg section into abutment with the distal end 134 of the first section 122 as clearly shown in FIG. 20. That action forms a somewhat triangularly shaped configuration at the portion of the device 120 which is located distally of the second pivotable joint.

The particular triangular shape of the distal portion of the device 120 is adjustable since top leg section 124 can be moved or slid with respect to the second pivotable joint, and since that joint is formed by the portion of the filament 128 extending through the intermediate opening 174 in the bottom leg section. Significantly, the second pivotable joint is releasable, so that it can be released during the removal mode of operation, as will be discussed shortly. Thus, by using one or more graspers the surgeon or other medical personnel using the device 120 can configure the shape of its triangular distal portion to his/her liking for the particular lifting task at hand.

Irrespective of the particular triangular shape of the distal end of the device 120, the top surface of the first section and the top surfaces of a portion of at least one of the distal end of the top leg section 124 and the distal end of the bottom leg section 126 form what can be called the device's liver support surface.

The device 120 is now ready to be used to lift or elevate the liver 8 toward the abdominal wall 4. To that end, one or more of the graspers can be used to move and orient the device's liver support surface under the liver to a desired position. For example, one grasper can be used to grasp the extending tassel 176 at the distal end of the first section 122 while another grasper grasps the filament 128 proximally of the second pivotable joint. Alternatively, the filament loop 162 on the top leg section 124 adjacent the first pivotable joint may be grasped by one grasper and the extending tassel 76 grasped by another grasper to carry the liver support surface to the desired position under the liver. Once the device is in that position, a needle or other piercing instrument (not shown), preferably including a grasper, can then be inserted from outside the patient through the patient's abdominal wall 4 into the patient's abdominal cavity 6 adjacent the liver 8. The device is now ready for the lifting mode of operation. To that end, a grasper of the piercing instrument can then be used to grasp a portion of the filament located proximally of the second pivotable joint to pull it through the aperture in the abdominal wall created by the piercing instrument, whereupon the proximal end portion of the filament is located outside of the patient. That proximal end portion can then be pulled or drawn to bring the top surface 164 at the proximal end of the bottom leg section 126 into engagement with a portion of the inner surface of the abdominal wall 4 with the intermediate portion of the filament located between the liver support surface and the proximal end of the bottom leg section causing the liver support surface to lift the liver towards the abdominal wall. Continued drawing or pulling of the proximal end portion of the filament from outside the patient will draw the distal portion of the device 120 closer to the abdominal wall to thereby elevate or lift the liver to its desired elevated or retracted position.

If, after or during, the elevation of the liver it is desired to provide more working room around the liver or to provide optimal visualization, the user can alter or adjust the shape of the distal portion of the device 120 so that the portions of the top leg section and/or bottom leg section which is/are not under the liver don't reduce the working room or deter good visualization. That adjustment action can be readily accomplished by grasping the filament loop 162 to move the top leg section 124, to which that loop is connected, to a desired position with respect to the bottom leg section 126.

Once the liver is at the desired elevated position with the shape of the distal portion of the device as desired, the proximal portion of the filament that is located outside the patient can be locked in place by any suitable means, e.g., a clamp 14A, to ensure that the liver remains held at that elevated position.

When it is desired to lower the liver back to its normal position, all that is required is to unsecure the proximal portion of the filament, e.g., remove or otherwise release the clamp 14A, to free the filament and thus enable it to be drawn back into the abdominal cavity by the weight of the liver on the liver support surface of the device and/or by grasping some portion of the device by a grasper and pulling it downward, whereupon the liver will be again located its normal position.

The device a20 is now ready to be removed from the abdomen during the removal mode of operation. That operation is accomplished as follows. A grasper is used to grasp the portion of the filament that is within the insufflated abdominal cavity immediately adjacent the aperture in the patient's abdominal wall through which the proximal portion of the filament extends. That grasped portion of the filament can then be pulled downward towards the patient's stomach to draw the proximal portion of the filament which had been located outside the patient's body back into the abdominal cavity. A grasper can now be introduced from outside the patient's body through a lumen in a trocar extending into the insufflated abdominal cavity to grasp the distal end of the filament, i.e., the tassel 176, and pull it into the distal end entryway of lumen of that trocar, whereupon the distal end 134 of the first section 122 will engage the distal end entryway of the lumen. Continued pulling of the tassel 176 through the lumen of the trocar will drag the first section 122 into the lumen, whereupon it will bend or flex into a generally linearized orientation so that it can pass out of the lumen at the proximal end thereof. The pulling of the first section 122 of the device through and out of the trocar results in the sliding of the filament 128 through the opening 172 in the distal end of the bottom leg section, so that the distal end of the bottom leg section separates from the distal end of the first section.

When the distal end of the top leg section 124 reaches the distal entryway of the lumen in the trocar, the top leg section 124 will pivot about the axis of the first pivotable joint so that the top leg section becomes collinear with the linearized first section that is in the lumen. Continued drawing of the device 120 out of the trocar eventually brings a portion of the bottom leg section 126 at the second pivotable joint into engagement with the distal end entryway of the lumen. Further drawing of the device out of the trocar causes the filament extending through the intermediate opening 174 in the bottom leg section to slide down the slot 156 until it reaches the end of the slot. Further drawing of the device out of the trocar causes the knot or bulbous end 178 at the proximal end of the filament 128 to reach the enlarged opening 158 in that slot, whereupon the knot or bulbous end 178 passes through the opening and thus out of the slot. That action results in the disconnection of the second pivotable joint, and results in the separation of the bottom leg section 124 from the top leg section 126 with the knot or bulbous end 178 of the filament 128 eventually reaching the intermediate opening 174 in the bottom leg section, whereupon the knot or bulbous end becomes stuck. Thus, while the bottom leg section will be separated from the top leg section it will nevertheless be connected to it by the portion of the filament between the top leg section and the bottom leg section as shown in FIG. 21. Moreover, the knot or bulbous end 178 of the filament will have carried the O-ring 130 off of the top leg section 124 onto the bottom leg section 126, wherein the O-ring will be trapped by the portion of the filament located between the distal end opening 172 of the bottom leg section and the intermediate opening 174 as shown in FIG. 22. Continued drawing of the device from the trocar will bring the bottom leg section into and through the lumen of the trocar until it exits the proximal end of the lumen, whereupon the entire device 120 will be out of the patient's body.

During the removal mode of operation one or more graspers can be used to hold or orient portions of the device to facilitate their entry into the lumen of the trocar used for removal of the device. In any case, as should be appreciated from the foregoing, the entire device 120 can be removed as a single unit from the patient's abdomen by merely pulling on the distal end, e.g., the tassel 176, of the filament, thereby providing a quick, easy and safe means of removal without the risk of any portions of the device being left within the patient's abdomen.

It should be pointed out at this juncture that the intra-abdominal liver retraction device 120 and method of use disclosed above are merely exemplary of various devices and methods that can be constructed and used in accordance with this invention. Thus, various modifications can be made to that device and to its method of use. For example, the first section need not be of a generally Z or undulating shape, but could be of any shape that provides a liver support surface sufficiently strong to support and elevate the liver, and which can be linearized to pass through an instrument port during the insertion and removal modes of operation. Moreover, the filament need not include a tassel at the distal end thereof to serve as a means for grasping the distal end portion of the first section. Further still the second section need not include the loop projection to enable that section to be readily grasped, but can include some other structure forming a grasping surface. Further still, some means other than an O-ring can be used to hold the top and bottom leg sections together, but enable them to pivot with respect to each other so that the shape and configuration of the device can be adjusted as desired within the abdominal cavity of the patient. Further yet, other materials can be used in lieu of the exemplary materials used to make up the components as described above.

We claim:

1. An intra-abdominal liver retraction device for use in a patient, the patient having a liver, an abdomen, an abdominal wall and a diaphragm, said intra-abdominal liver retraction device comprising:
   a generally J or L shaped body including an elongated section, an intermediate section, and a foot section, said elongated section having a proximal end, said foot section extending at an angle to said elongated section, said foot section being configured to be brought to a position adjacent to a portion of the diaphragm of the patient, whereupon a portion of said elongated section and said foot section is disposed under a portion of the liver;
   a stabilizing member having a pair of ends disposed opposite each other, said stabilizing member being coupled to said proximal end and configured to be moved with respect thereto from a first orientation to a second orientation and vice versa, said stabilizing member when in said first orientation extending generally perpendicular to said elongated section, said stabilizing member when in second orientation extending generally parallel to said elongated section, said stabilizing member being configured to be brought into frictional engagement with a portion of the abdominal wall of the patient; and
   a flexible filament connected to said elongated section of said generally J or L shaped body, said flexible filament being configured to be drawn from within the abdomen through an aperture in the abdominal wall to cause said stabilizing member when in said second orientation to be brought into frictional engagement with a portion of the abdominal wall and also cause said elongated section and said foot section to lift the liver upward towards the abdominal wall.

2. The intra-abdominal liver retraction device of claim 1, wherein at least portions of said generally J or L shaped body are somewhat flexible, yet self-supporting and configured such that when said stabilizing member is in said second orientation said intra-abdominal liver retraction device can be bent into a somewhat linear shape for insertion through a trocar into the abdomen.

3. The intra-abdominal liver retraction device of claim 2, wherein said intermediate section is located between said elongated section and said foot section.

4. The intra-abdominal liver retraction device of claim 1, additionally comprising a swivel assembly coupled between said proximal end and said stabilizing member to enable said stabilizing member to be swiveled to either said first and second orientations.

5. The intra-abdominal liver retraction device of claim 1, wherein said stabilizing member is normally biased into said first orientation.

6. The intra-abdominal liver retraction device of claim 5, additionally comprising a spring for normally biasing said stabilizing member into said first orientation.

7. The intra-abdominal liver retraction device of claim 1, wherein said foot section is an elongated slightly concave member.

8. The intra-abdominal liver retraction device of claim 7, wherein said elongated section has a predetermined maximum width, wherein said stabilizing member is an elongated member having a predetermined maximum width, wherein said foot section has a predetermined maximum width, and wherein the predetermined maximum width of said elongated section, the predetermined maximum width of said stabilizing member and the predetermined maximum width of said foot section, are each sufficiently small to pass through a conventional trocar or other access port instrument into the abdomen.

9. The intra-abdominal liver retraction device of claim 1, wherein said J or L shaped body is an integral unit.

10. The intra-abdominal liver retraction device of claim 9, wherein J or L shaped body comprises nylon or polycarbonate.

11. The intra-abdominal liver retraction device of claim 1, wherein said stabilizing member includes a first opening located adjacent one of said pair of ends, and a second opening located adjacent another of said pair of ends, and wherein each of said openings is configured to be grasped by a grasping member to move said stabilizing member to said second orientation.

12. A method of lifting the liver of a patient, the patient having an abdomen, an abdominal wall having an inner surface, and a diaphragm, said method comprising:
   providing an intra-abdominal liver retraction device comprising a generally J or L shaped body, a stabilizing member, and a flexible filament, said generally J or L shaped body including an elongated section, an intermediate section, and a foot section, said elongated section having a proximal end, said foot section extending at an angle to said elongated section, said stabilizing member having a pair of ends disposed opposite each other and being coupled to said proximal end and configured to be moved with respect thereto from a first orientation to a second orientation and vice versa, said stabilizing member when in said first orientation extending generally perpendicular to said elongated section, said stabilizing member when in second orientation extending generally parallel to said elongated section, said flexible filament being connected to said elongated section;
   introducing said intra-abdominal liver retraction device with said stabilizing member orientated in said second orientation through a port in the abdominal wall into the abdomen;
   causing said stabilizing member to be oriented in said first orientation when said intra-abdominal liver retraction device is within the abdomen;
   causing said foot section to be brought to a position adjacent a portion of the diaphragm and with a portion of said elongated section being disposed under the liver and with at least a portion of said foot section disposed under the liver; and
   drawing said flexible filament through an aperture in the abdominal wall from outside the abdomen to bring said stabilizing member into frictional engagement with a portion of the inner surface of the abdominal wall and to cause said elongated section and said foot section to lift the liver upward towards the abdominal wall.

13. The method of claim 12, wherein said intra-abdominal liver retraction device is introduced through a small port into the abdomen by use of a trocar extending through said port.

14. The method of claim 13, wherein said generally J or L shaped body is somewhat flexible, yet self-supporting and wherein said method comprises:
bending said generally J or L shaped body into a somewhat linear shape for insertion through said trocar into the abdomen.

15. The method of claim 13, additionally comprising:
swiveling said stabilizing member to said second orientation from within the abdomen to enable said intra-abdominal liver retraction device to be withdrawn from the abdomen via a trocar.

16. The method of claim 15, additionally comprising:
grasping a portion of said stabilizing member by a grasping tool inserted through a trocar to swivel said stabilizing member to said second orientation and pulling said intra-abdominal liver retraction device out of the abdomen through said trocar.

17. The method of claim 16, wherein said stabilizing member includes a first opening located adjacent one of said pair of ends, and a second opening located adjacent another of said pair of ends, and wherein said method comprises:
grasping one of said openings of said stabilizing member by said grasping tool to swivel said stabilizing member to said second orientation.

18. The method of claim 12, additionally comprising:
piercing the abdominal wall from outside thereof to form said aperture;
introducing a grasping instrument through said aperture into the abdomen to grasp a portion of said flexible filament; and
drawing said portion of said filament through said aperture to a position outside the abdominal wall to apply tension to said filament.

19. The method of claim 18, additionally comprising releasably securing a clip to a portion of said filament outside the abdominal wall to maintain tension on said filament.

20. The method of claim 19, additionally comprising:
releasing said clip from said portion of said filament outside said abdominal wall, thereby releasing the tension on said filament; and
grasping a portion of said stabilizing member by a grasping tool inserted through a trocar to swivel said stabilizing member to said second orientation and pulling said intra-abdominal liver retraction device out of the abdomen through said trocar.

21. An intra-abdominal liver retraction device for use in a patient, the patient having a liver, an abdomen, an abdominal wall and a diaphragm, said intra-abdominal liver retraction device being configured to be introduced into the abdomen via an instrument port extending through the abdominal wall during an insertion mode of operation, said intra-abdominal liver retraction device comprising:
a first section and a second section secured together at a first pivotable joint, said first section configured to be flexed into a generally linear elongated shape during an insertion mode of operation, said first section having a distal end and a proximal end, said second section having a generally linear elongated shape;
a third section having a generally linear shape and being pivotably connected to said second section by a second pivotable joint, whereupon said third section extends parallel to said second section, said second pivotable joint being releasable, said second and said third sections being configured to extend parallel to each other and substantially collinearly with said first section during said insertion mode of operation; and a flexible filament having a distal end portion, an intermediate portion, and a proximal end portion, said distal end portion being secured to said distal end of said first section, said intermediate portion being located between said distal end portion and said proximal end portion and being configured to be pulled during a deployment mode of operation to cause said third section to pivot with respect to said second section at said second pivotable joint whereupon said second section and said third section extend at an angle to each other with a distal end of said third section being immediately adjacent said distal end of said first section, whereupon a portion of said first section and a portion of at least one of a distal end of said second section and said distal end of said third section form a liver support surface configured to be disposed under a portion of the liver to lift the liver during a lifting mode of operation.

22. The intra-abdominal liver retraction device of claim 21, wherein said intermediate portion of said filament extends out of an opening in said third section located between said distal end of said third section and a proximal end of said third section, said proximal end portion of said filament being configured to be extended through an aperture in the abdominal wall and pulled from outside the patient when said liver support surface is located under the liver to cause a proximal end of said third section to be in engagement with an inner surface portion of the abdominal wall and with said intermediate portion of said filament located between said liver support surface and said proximal end of said third section to lift the liver towards the abdominal wall during said lifting mode of operation.

23. The intra-abdominal liver retraction device of claim 22, wherein said intra-abdominal liver retraction device is configured to be removed from the abdomen during a removal mode of operation by grasping said distal end portion of said filament to pull said distal end of said first section into an instrument port extending into the abdominal cavity, whereupon said first section becomes linearized to pass into and through the instrument port followed by said second section, and thereafter followed by said third section which separates from said second section but is coupled to said second section by a portion of said filament so that said third section also passes through the instrument port.

24. The intra-abdominal liver retraction device of claim 23, wherein the first section has a generally Z or undulating shape.

25. The intra-abdominal liver retraction device of claim 23, wherein said second section additionally comprises a flexible projection configured to be grasped by a grasping instrument to adjust the position of said second and third sections with respect to each other.

26. The intra-abdominal liver retraction device of claim 23 wherein the position of said third section can be adjusted with respect to said second section.

27. The intra-abdominal liver retraction device of claim 23, wherein said second section is a top leg section and said third section is a bottom leg section disposed under said top leg section, said top leg section having a proximal end and a slot interposed between said distal end of said top leg section and said proximal end of said top leg section, said bottom leg section including a distal opening at said distal end thereof, an intermediate opening located between said distal opening of said bottom leg section and said proximal end of said bottom leg section, said intermediate opening of said bottom leg section intersecting said slot of said top section at a movable intersection, said filament extending through said distal opening in said bottom leg section.

28. The intra-abdominal liver retraction device of claim 27, wherein said filament includes a portion extending through said movable intersection to form said second pivotable joint and wherein the position of said third section can be adjusted with respect to said second section at said second pivotable joint.

29. The intra-abdominal liver retraction device of claim 28, wherein said proximal end portion of said filament is bulbous and wherein said slot includes an enlarged opening adjacent a proximal end of said slot, said enlarged opening being of a sufficient size to permit said bulbous proximal end portion of said filament to pass therethrough to enable said bottom leg section to separate from said top leg section and to trail said top leg section through the instrument port.

30. The intra-abdominal liver retraction device of claim 29, additionally comprising a ring of flexible material extending about contiguous portions of said top leg section and said bottom leg section slightly proximally of second pivotable joint to hold said contiguous portions together during said insertion, deployment and lifting modes of operation.

31. The intra-abdominal liver retraction device of claim 30, wherein said ring of flexible material is trapped to said bottom leg section by a portion of said filament extending through said distal opening of said bottom leg section and through said intermediate opening in said bottom leg section after said bottom leg section has been separated from said top leg section, whereupon said ring of flexible material is removed from the abdomen with the removal of said intra-abdominal liver retraction device from the abdomen during said removal mode of operation.

32. The intra-abdominal liver retraction device of claim 23, wherein said distal end portion of said filament extends through an opening in said distal end of said top leg section to form a grasping portion configured to be grasped by a grasping instrument to pull said distal end of said first section into the instrument port.

33. A method of lifting the liver of a patient, the patient having a liver, an abdominal cavity, an abdominal wall, and a diaphragm, said method comprising:

providing an intra-abdominal liver retraction device comprising a first section, a second section, a third section and a flexible filament, said first and second sections being secured together at a first pivotable joint, said first section having a distal end and a proximal end, said second section having a generally linear elongated shape, said third section having a generally linear shape and being pivotably connected to said second section by a second pivotable joint, whereupon said third section extends parallel to said second section, said second pivotable joint being releasable, said second and said third sections being configured to extend parallel to each other, said flexible filament coupling said first, second and third sections together and having a distal end portion and a proximal end portion, said distal end portion being secured to said distal end of said first section;

disposing said second and third sections so that they are substantially parallel to each other and pivoting said first member about said first pivotable joint so that said second and third sections are substantially collinear with said first section;

introducing said first section through an instrument port extending through the abdominal wall into the abdominal cavity during an insertion mode of operation to cause said first section to readily pass through said instrument port followed by said second and third sections;

grasping portions of said intra-abdominal liver retraction device and pulling said proximal end portion of said filament during a deployment mode of operation to cause said third section to pivot with respect to said second section at said second pivotable joint whereupon said second section and said third section extend at an angle to each other with a distal end of said third section being immediately adjacent said distal end of said first section and with a portion of said first section and a portion of at least one of a distal end of said second section and said distal end of said third section forming a liver support surface; and disposing at least a portion of said liver support surface under a portion of the liver to lift the liver during a lifting mode of operation.

34. The method of claim 33, wherein said method comprises drawing said proximal portion of said filament through an aperture in the abdominal wall from outside the patient so that a portion of said filament is located outside of the patient wherein said filament brings said proximal end of said third section into engagement with an inner surface portion of the abdominal wall, with said intermediate portion of said filament located between said liver support surface and said proximal end of said third section to thereby lift the liver towards the abdominal wall to an elevated position during said lifting mode of operation.

35. The method of claim 34, additionally comprising holding said proximal portion of said filament that is located outside the patient in place to hold the liver at said elevated position.

36. The method of claim 35, additionally comprising releasing said proximal portion of said filament that is located outside the patient to lower the liver from said elevated position to a lowered position.

37. The method of claim 33, additionally comprising removing said intra-abdominal liver retraction device from the abdominal cavity of the patient during a removal mode of operation.

38. The method of claim 37, wherein said removal mode of operation is accomplished by grasping said distal end portion of said filament to pull said distal end of said first section into an instrument port extending into the abdomen, whereupon said first section passes into and through the instrument port followed by said second section, and thereafter followed by said third section which separates from said second section but is coupled to said second section by a portion of said filament so that said third section also passes through the instrument port.

39. The method of claim 34, wherein said first section comprises a generally Z or undulating shaped member, which is configured to be linearized when passing through said instrument port during said insertion mode of operation and during said removal mode of operation.

40. The method of claim 39, wherein said instrument port comprises a 12 mm trocar.

* * * * *